United States Patent
Gambetta (12)

(10) Patent No.: US 6,207,433 B1
(45) Date of Patent: Mar. 27, 2001

(54) POLYPEPTIDES HAVING AMINOLEVULINIC ACID ACTIVITY AND NUCLEIC ACIDS ENCODING SAME

(75) Inventor: Greg Gambetta, Davis, CA (US)

(73) Assignee: Novo Nordisk Biotech, Inc., Davis, CA (US)

( * ) Notice: Subject to any disclaimer, the term of this patent is extended or adjusted under 35 U.S.C. 154(b) by 0 days.

(21) Appl. No.: 09/477,472

(22) Filed: Jan. 4, 2000

Related U.S. Application Data

(62) Division of application No. 09/193,107, filed on Nov. 16, 1998, now Pat. No. 6,033,892.
(60) Provisional application No. 60/066,107, filed on Nov. 17, 1997.

(51) Int. Cl.⁷ .................................................. C12N 9/10
(52) U.S. Cl. .................... 435/193; 435/183; 530/350; 530/371; 536/23.2
(58) Field of Search .................................. 435/193, 183; 530/371, 350; 536/23.2

(56) References Cited

U.S. PATENT DOCUMENTS

| 4,902,620 | 2/1990 | Bard et al. . | |
|---|---|---|---|
| 5,871,991 | * 2/1999 | Elrod et al. .......................... | 435/193 |

FOREIGN PATENT DOCUMENTS

| 0 505 311 | 9/1992 | (EP) . |
|---|---|---|
| WO 93/19195 | 9/1993 | (WO) . |
| WO 97/47746 | 12/1997 | (WO) . |

OTHER PUBLICATIONS

Bradshaw et al., Curr Genet. vol. 23, pp. 501–507 (1993).

* cited by examiner

*Primary Examiner*—Ponnathapu Achutamurthy
*Assistant Examiner*—Richard Hutson
(74) *Attorney, Agent, or Firm*—Robert L. Starnes; Elias Lambiris, Esq.

(57) ABSTRACT

The present invention relates to isolated polypeptides having 5-aminolevulinic acid synthase activity and isolated nucleic acid sequences encoding the polypeptides. The invention also relates to nucleic acid constructs, vectors, and host cells comprising the nucleic acid sequences as well as methods for producing and using the polypeptides.

17 Claims, 14 Drawing Sheets

```
1    GAATTCATCGTACGAGACGGTTGGTATAAAGCCGAGAGAGCAGAGTATTTGGACGTGGGGA    60
61   TATCTGAGTTTGACATTTTGAGATACCTATGAAGAGACGAGCTAAAGGATTGATCATAAA    120
121  GTACATTGCCAATACTACTTACTGTACAATTAGGTTTTTTTGTGACTTGTTCATTGTAAG    180
181  ACACTTGTCCGCCTTTCGATAACCATTCAACAATACTCAACCAATGGTGTAAAGCTGTC    240
241  AAGGGTCTAAAGGCTAAAAGTACGACTGCAACGTGCATGAACAGAACGAGCCAATCAAGG    300
301  GCAATGTATTTCTCTACAGCCGTCCCTGAGTTTGACTCGGGCGGTTTCGTCCCTGTACGA    360
361  TTGCCGAGCGTTGTACGTGCGGACTTGGAACTCAAGGTTGCGGGCCGCAGCATGGCCGC    420
421  AACTTGACAATCTTTTCGCCGAGGTCATTCTGTTTCCGAGTTTTTTTATTTTATGTTG    480
481  AGTTAATAAGAGGGTCAGGACTTCAACTAGTCAGTTAGTTCGTTTATGCGGAAACGTTTA    540
541  CGGCGGTTGTAGATACAGAAAGTAAATCAACGGGTCAAACGCTTCACGTGTCAGATCATT    600
601  ATTTACAAACCCCGCTGTCTAGGCCTTACAGCCAGCATCGGGCCTGCATGCGACAAGA    660
661  ATGTACCATAGACTTGCCTAGAAGGGAAATTTGAGCGGAGTTAGTTGAGAAGAACAGAA    720
721  GAAAATGGACGGAATCGAAACGGAAGTAATTTATGGTCAATGACCGACCGTTCTTGCCG    780
```

```
 781  AGCCATGGACCACCGACTTATTCAATCCTCTCTTTACGGTCATCTATCTACCGCTTTATT                                    840
 841  ATCCTCCTTCTTCATATTTCCCTCCTCTTCTTTTTCCTTTTTACACTCAACCTCAACC                                      900
 901  TCAACCCGCCTCTCCCTCACTTGCAAAAGCTCAATTGCTTTTGCCTTCGCCTCGTTCG                                      960
 961  CTCTCGGCGATCGAGTGTAAGCCCCCTCGCTTTTTTTTTTATTCACCTGGCATATTGCCCC                                  1020
1021  TCCAAGTTCAAACTACCACGTTTGCCCCCTCGCTTTACGAAAGCATTGCTATCG                                         1080
1081  CAACTTGACCCTGTGCCACCAAATACACGTAACA ATG GAT GCT GTT CTT CGC CAG                                 1034
                                         M   D   A   V   L   R   Q

1135  TCC AAG GCC ATG TGC CCT TTT ATG AAG ACG GCC ACT CCC GCC ACT                                   1179
       S   K   A   M   C   P   F   M   K   T   A   T   P   A   T

1180  CTG CGC GCC TTG TCA ACT TCG TCT CGC GCC CTT CCG GCT CCT GCC                                   1224
       L   R   A   L   S   T   S   S   R   A   L   P   A   P   A

1225  TCG CCA TGT GGA GGC ACC ATG TCG AAG CTG CAG CTT CTT GGT CAG                                   1269
       S   P   C   G   G   T   M   S   K   L   Q   L   L   G   Q

1270  CGA TGC CCC GTC ATG G GTAAGGCATGGCTGTTCAGACCGCCAAGAACCGGCTG                                   1323
       R   C   P   V   M
```

```
1324  CTGGCTCTCTGTTCGTGCCTTCTCCAACCACTCCAAGACTGGAAAGGCCAAGATTCATACTT  1383

1384  CCAG CA ACA AGG AGG CTC GTG CTG TTG AAC GCC CAC TCT TCG AAG    1428
           A   T   R   R   L   V   L   L   N   A   H   S   S   K

1429  GCC GCG ACA ATG GTA TGT TCG AAT CCC A GTAAAATCTGTGTTACTTCTTTC  1478
       A   A   T   M   V   C   S   N   P

1479  CGTCACTTGATTGTATCTAATCTTGCGCCCAG CT CCT CCT GGT ATT CAC GCG    1530
                                       T   P   P   G   I   H   A

1531  AAC CGA AAG GCC GCA TCC GCA ACC GCT TCC TAT GAA ACC TTT TAC   1575
       N   R   K   A   A   S   A   T   A   S   Y   E   T   F   Y

1576  GCT GGC TTC CAA TCT CCT GGC AAA TTC CAC AAG GAT AAA TCC TAC   1620
       A   G   F   Q   S   P   G   K   F   H   K   D   K   S   Y

1621  AAC ACT GAG CTC AAT ATC AAC CGT TTG GCA AAG GAG TTT CCG CGT   1665
       N   T   E   L   N   I   N   R   L   A   K   E   F   P   R

1666  TTC AAC AAT ATC AAC CGT TTG GCA AAG GAG GAT CGA GTA ACT GTC   1710
       F   N   N   I   N   R   L   A   K   E   D   R   V   T   V

1711  ATG TCT GAC AAG GAG GAT CGA GTA ACT GTC TGG TGC GCC AAC GAC   1755
       M   S   D   K   E   D   R   V   T   V   W   C   A   N   D
```

Fig. 1C

| | | | | | | | | | | |
|---|---|---|---|---|---|---|---|---|---|---|
| 1756 | TAC Y | CTT L | GGC G | ATG M | GGC G | CGC R | AAT N | CCC P | CAT H | GTT V | CTC L | AAC N | ACG T | ATG M | CAC H | 1800 |
| 1801 | AAA K | ACC T | TTG L | GAG E | GAA E | TAT Y | GGT G | GCT A | GGT G | GCG A | GGC G | ACT T | CGA R | AAC N | 1845 |
| 1846 | ATC I | TCT S | GGT G | CAC H | AAC N | AAG K | GAT D | AGC S | GTT V | GAG E | CTG L | GCT A | ACA T | CTG L | 1890 |
| 1891 | GCC A | AAG K | CTT L | CAC H | AAC N | GCC A | AAG K | GAT D | AGC S | GCT A | CTT L | GTG V | TTC F | AGC S | TCT S | TGC C | 1935 |
| 1936 | TAT Y | GTT V | GCC A | AAC N | GAC D | GCA A | ACC T | CTG L | GCG A | ACA T | CTC L | AAC N | CAC H | GCC A | AGC S | AAG K | TTG L | 1980 |
| 1981 | CCC P | GAA E | TGC C | GTT V | ATT I | CTT L | TCC S | GAT D | AGC S | TTG L | GGC G | ACC T | TTC F | AAG K | ATT I | GTT V | TTC F | AAG K | 2025 |
| 2026 | ATC I | CAG Q | GGA G | ATC I | CGA R | CAC H | TCT S | GAG E | GCC A | AAG K | CTG L | GCT A | TCT S | ATG M | 2070 |
| 2071 | CAC H | AAC N | GAT D | GTG V | CAG Q | GAC D | CTC L | GAG E | GCC A | AAG K | CTG L | GCT A | TCG S | CTA L | CCC P | 2115 |

Fig. 1D

| | | | | | | | | | | | | | | |
|---|---|---|---|---|---|---|---|---|---|---|---|---|---|---|
|2116|CTA<br>L|CAC<br>H|GTG<br>V|CCT<br>P|AAG<br>K|ATC<br>I|ATA<br>I|GCT<br>A|TTC<br>F|GAG<br>E|TCG<br>S|GTG<br>V|TAC<br>Y|AGT<br>S|ATG<br>M|2160|
|2161|TGC<br>C|GGC<br>G|TCC<br>S|ATT<br>I|GGT<br>G|GCC<br>A|ATC<br>I|ACT<br>T|TTT<br>F|CCT<br>P|ATT<br>I|GAG<br>E|GAA<br>E|ATC<br>I|GAC<br>D|CTT<br>L|GAT<br>D|GCC<br>A|GAC<br>D|2205|
|2206|AAG<br>K|TAT<br>Y|GGC<br>G|GCC<br>A|ATC<br>I|ACT<br>T|TTT<br>F|CTT<br>L|GAT<br>D|GAA<br>E|GTC<br>V|CAT<br>H|GCC<br>A|GTC<br>V|GGC<br>G|2250|
|2251|ATG<br>M|TAC<br>Y|GGT<br>G|CTT<br>L|CAT<br>H|GCC<br>A|GGT<br>G|GCT<br>A|GTT<br>V|GCT<br>A|GAG<br>E|CAC<br>H|CTT<br>L|GAC<br>D|TGG<br>W|2295|
|2296|GAA<br>E|GCC<br>A|CAT<br>H|GCC<br>A|AAC<br>N|GGT<br>G|GCC<br>A|CTT<br>L|CGC<br>R|GGG<br>G|ACC<br>T|ATC<br>I|ATG<br>M|GAC<br>D|CGA<br>R|2340|
|2341|ATC<br>I|GAC<br>D|ATT<br>I|ATC<br>I|ACT<br>T|GGT<br>G|ACT<br>T|CTG<br>L|GGC<br>G|AAG<br>K|TAC<br>Y|GCG<br>A|TAC<br>Y|GGT<br>G|TGC<br>C|GTC<br>V|2385|
|2386|GGT<br>G|GGC<br>G|TAT<br>Y|ATC<br>I|GCT<br>A|GGT<br>G|AGC<br>S|GCC<br>A|AAG<br>K|TTC<br>F|ATT<br>I|GAC<br>D|GTG<br>V|ATC<br>I|CGA<br>R|2430|
|2431|TCG<br>S|TTG<br>L|GCC<br>A|CCC<br>P|GGC<br>G|TTC<br>F|ATC<br>I|TTC<br>F|ACT<br>T|ACT<br>T|TCT<br>S|TTG<br>L|CCT<br>P|CCT<br>P|GCT<br>A|2475|

Fig. 1E

```
2476  ACC ATG GCT GGT GCC CAA ACC TCT ATT GAG TAC CAG ATG GAG TAC  2520
       T   M   A   G   A   Q   T   S   I   E   Y   Q   M   E   Y

2521  GAT GGC GAC CGA CGA CTC CAG CAG CTG CAC ACT CGT GCT GTC AAG  2565
       D   G   D   R   R   L   Q   Q   L   H   T   R   A   V   K

2566  GAG GCT ATG AAC GCT CGC GAC ATC CCT GTC ATC CCC AAT CCC TCT  2610
       E   A   M   N   A   R   D   I   P   V   I   P   N   P   S

2611  CAC ATC ATT CCT GTA CTA GTT GGT GGC AAC GCC GAG ACC AAG GCG  2655
       H   I   I   P   V   L   V   G   G   N   A   E   T   K   A

2656  GCT TCC GAC ATG CTT CTC AAC GAC TAC GGA ATT TAT GTC CAA TCC  2700
       A   S   D   M   L   L   N   D   Y   G   I   Y   V   Q   S

2701  ATC AAC TAC CCC ACC GTT CCA GTT GGT CAG GAG CGT CTT CGC ATC  2745
       I   N   Y   P   T   V   P   V   G   Q   E   R   L   R   I

2746  ACC CCT ACC CCC GGC CAT GTC AAG GAG TAC CGC AAC CAG CTT GTC  2790
       T   P   T   P   G   H   V   K   E   Y   R   N   Q   L   V

2791  GAG GCT GTT GAT GAG ATC TGG ACT CGC CTC AAC ATC AAG CGA ACC  2835
       E   A   V   D   E   I   W   T   R   L   N   I   K   R   T
```

Fig. 1F

| | | | | | | | | | | | | |
|---|---|---|---|---|---|---|---|---|---|---|---|---|
| 2836 | TCC S | GAC D | TGG W | GCT A | GCC A | GAG E | GGT G | GGC G | TTT F | ATT I | GGT G | GTC V | GGC G | GAG E | GAG E | 2880 |
| 2881 | AGC S | AAC N | GTA V | CAG Q | AAC N | CCT P | CTT L | TGG W | ACT T | GAC D | AAG K | CAA Q | CTC L | AAC N | GTT V | 2925 |
| 2926 | GAG E | CAG Q | GCT A | ACG T | AAG K | GAG E | ATC I | AAG K | GCC A | ACC T | GGT G | CAA Q | GCC A | GCC A | AAT N | 2970 |
| 2971 | GGT G | ATT I | ACT T | GAG E | GCG A | CTT L | CTC L | GAG E | CTT L | GAG E | ATT I | AAG K | CAA Q | TCC S | TCC S | 3015 |
| 3016 | GAG E | GTC V | GCT A | ACT T | GCT A | GCT A | TAAGCGTAAGATATACTCAGCACCTTACGCGCACT | | | | | | | | | 3068 |
| 3069 | GCCATCATAGGTGAAAGATGAGCAGTTCCAGTTCACTTCTATGATAACCATTTGAGAT | | | | | | | | | | | | | | | 3127 |
| 3128 | ATCTTTTATCATTTATGCTATCCATTGGATATGTAAATTGAATTATTTTACGTCCATT | | | | | | | | | | | | | | | 3186 |
| 3187 | ACCACACATGACGTGGTATATGGAGCAACTGCAACTTTAGTCTCTCCACTATTCTGTGA | | | | | | | | | | | | | | | 3245 |
| 3246 | TGTTAATGAAATGCTGCTCTCATGACACCTGACCAATTGTATGGAAACGATACTCTGA | | | | | | | | | | | | | | | 3304 |
| 3305 | CATTGTTGCATTTTAAACCGGAACAATGTTTGCCGATAATGAAGTGAGGAAGGTTGCA | | | | | | | | | | | | | | | 3363 |

Fig. 1G

| | | |
|---|---|---|
| 3364 | GGGATGACCGGCCCTCCACAGAACCGGAGCAACGGCGAGATTTCGAGGCCCGGGTCCGTT | 3422 |
| 3423 | TCTAGTGACAGGATCCCTGCATATCAACAACTTCAGACCAGTCAAAGAGCGCTCGAGAC | 3481 |
| 3482 | GACCAGGGTCAACAGAATATTGATCAATGTCTGGGATGTCGCCCGTTTTCAACTCCGTC | 3540 |
| 3541 | TCCTTTTCAAACTGCTCAATCTCTGTGAGACAAGCACACTCAGATACCTAAGTCGTGAC | 3599 |
| 3600 | AAGATGAGTCCTGGCTCAGCTCAAGCTAAGAACAAGGGCCCAAAGCATGCACAACATG | 3658 |
| 3659 | CGCTAAGGCTAAGGCAAGATGCGGTCCCCGGCCCTCTTGGGAGCCTCAAGTGCCGACAGGT | 3717 |
| 3718 | AAGTCATGATAATTGGTTCATTTTTGGGAATATCTTGATGGCTTGCGTTTAATCGTCGC | 3776 |
| 3777 | CGTACCAGGCTTGTCTTGTACCATATACACATATGTGGTGTGAGTTGGTGGAGAGGTACAT | 3835 |
| 3836 | ATGCTGACATTAGAATTC | 3853 |

Fig. 1H

SEQUENCE LISTING

<160> NUMBER OF SEQ ID NOS: 12

<210> SEQ ID NO 1
<211> LENGTH: 3853
<212> TYPE: DNA
<213> ORGANISM: Fusarium

<400> SEQUENCE: 1

```
gaattcatcg tacgagacgg ttggtataaa gccgagagca gagtattttg gacgtgggga      60
tatctgagtt tgacattttg agatacctat gaagagacga gctaaaggat tgatcataaa     120
gtacattgcc aatactactt actgtacaat taggtttttt tgtgacttgt tcattgtaag     180
acacttgtcc gcctttcgat aaccattcaa caatactcaa ccaatgggtg taaagctgtc     240
```

-continued

```
aagggtctaa aggctaaaag tacgactgca acgtgcatga acagaacgag ccaatcaagg      300
gcaatgtatt tctctacagc cgtccctgag tttgactcgg gcggtttcgt ccctgtacga      360
ttgccgagcg ttgtacgtgc ggactttgga actcaaggtt gcgggccgca gcatggccgc      420
aacttgacaa tcttttttcgc cgaggtcatt ctgtttccga gttttttttta ttttatgttg    480 agttaataag agggtcagga cttcaactag tcagttagtt cgtttatgcg gaaacgttta      540
cggcggttgt agatacagaa agtaaatcaa cgggtcaaac gcttcacgtg tcagatcatt      600
atttacaaac cccgctgtct aggccttaca gccagcatcg gggcctgcat ggcgacaaga      660
atgtaccata gacttgccta aaggggaaa tttgagcgga gttagttgag aagaacagaa       720
gaaaatggac ggaatcgaaa cggaagtaat ttatgggtca atgaccgacc gttcttgccg      780
agccatggac caccgactta ttcaatcctc tctttacggt catctatcta ccgctttatt     840
atcctccttc ttcatatttt ccctccttct tcttttttcct ttttacactc aacctcaacc    900
tcaacccgcc tctcctcact tgcaaaagct caattgcttt tgcttcgcct cgcttgttcg     960
ctctcgcgat cgagtgtaag cccctcgctt tttttttttat tcacctggca tatttgcccc   1020
tccaagttca aactaccacg ttttgcccct ctggttcgct ttacgaaagc attgctatcg    1080
caacttgacc tgtgccacca aatacacgta acaatggatg ctgttcttcg ccagtccaag    1140
gccatgtgcc cttttatgaa acggccact cccgccactc tgcgcgcctt gtcaacttcg     1200
tctcgcgccc ttccggctcc tgcctcgcca tgtggaggca ccatgtcgaa gctgcagctt    1260
cttggtcagc gatgccccgt catgggtaag gcatggctgt tcagaccgcc aagaaccgcg    1320
ctgctggctc tgttcgtgcc ttctccaacc actccaagac tggaaaggcc aagattcata    1380
cttccagcaa caaggaggct cgtgctgttg aacgcccact cttcgaaggc cgcgacaatg    1440
gtatgttcga atcccagtaa aatctgttta cttctttccg tcacttgatt gtatctaatc    1500
ttgcgcccag ctcctcctgg tattcacgcg aaccgaaagg ccgcatccgc atccccaacc    1560
gcttccgctg ccgccgctgg cttccaatct cctggcaaat tcgactatga aaccttttac    1620
aacactgagc tcgagaagaa acacaaggat aaatcctacc gttacttcaa caatatcaac    1680
cgtttggcaa aggagtttcc gcgtgcacac atgtctgaca aggaggatcg agtaactgtc    1740
tggtgcgcca acgactacct tggcatgggc cgcaatcccc atgttctcaa cacgatgcac    1800
aaaaccttgg aggaatatgg tgctggtgcg ggcggtactc gaaacatctc tggtcacaac    1860
aagcacgccg ttgagctgga ggctacactg gccaagcttc acgccaagga tagcgctctt    1920
gtgttcagct cttgctatgt tgccaacgac gcaaccctgg cgacactcgg cagcaagttg    1980
cccgaatgcg ttattctttc cgatagcttg aaccacgcct ctatgatcca gggaatccga    2040
cactctggca ccaagaagat tgttttcaag cacaacgatg tgcaggacct cgaggccaag    2100
ctggcttcgc tacccctaca cgtgcctaag atcatagctt tcgagtcggt gtacagtatg    2160
tgcggctcca ttggtcctat tgaggaaatc tgtgatcttg ccgacaagta tggcgccatc    2220 actttcttg atgaagtcca tgccgtcggc atgtacggtc ttcatggtgc tggtgttgct    2280
gagcaccttg actgggaagc ccatgccaac ggtgcccttc gcgggaccat catggaccga    2340
atcgacatta tcactggtac tctgggcaag gcgtacggtt gcgtcggtgg ctatatcgct    2400
ggtagcgcca agttcattga cgtgatccga tcgttggccc ccggcttcat cttcactact    2460
tctttgcctc ctgctaccat ggctggtgcc caaacctcta ttgagtacca gatggagtac    2520
gatggcgacc gacgactcca gcagctgcac actcgtgctg tcaaggaggc tatgaacgct    2580
cgcgacatcc ctgtcatccc caatccctct cacatcattc ctgtactagt tggcaacgcc    2640
```

-continued

```
gagaccgcca aggcggcttc cgacatgctt ctcaacgact acggaattta tgtccaatcc    2700
atcaactacc ccaccgttcc agttggtcag gagcgtcttc gcatcacccc tacccccggc    2760
catgtcaagg agtaccgcaa ccagcttgtc gaggctgttg atgagatctg gactcgcctc    2820
aacatcaagc gaacctccga ctgggctgcc gagggtggct ttattggtgt cggcgaggag    2880
agcaacgtac agaaccctct tggactgac aagcaactca acgttgagca ggctacgaag    2940
gagatcaagg ccaccggtca agccgccaat ggtattactg aggcgcttct cgagcttgag    3000
attaagcaat cctccgaggt cgctactgct gcttaagcgt aagatatact cagcacctta    3060
cgcgcactgc catcataggt gaaagatgag cagttccagt tcacttctat gataaccatt    3120
ttgagatatc ttttatcatt tatgctatcc attggatatg taaattgaat tattttacg    3180 tccattacca catgacgtgg tatatggagc aactgcaact tttagtctct ccactatttc    3240
tgtgatgtta atgaaatgct gctctcatga cacctgacca atttgtatgg aaacgatact    3300
ctgacattgt tgcattttaa accggaacaa tgttttgccg ataatgaagt gaggaaggtt    3360
gcagggatga ccggcctcca cagaaccgga gcaacggcga gatttcgagg cccgggtccg    3420
tttctagtga caggatccct gcatatcaac aacttcagac cagtcaaaga gcgctcgaga    3480
cgaccagggt caacagaata ttgatcaatg tctgggatgc cgccgttttt caactccgtc    3540
tccttttcaa actgctcaat ctctgtgaga caagcacact cagataccta agtcgtgaca    3600
agatgagtcc tggctcagct caagctaaga caaggggcc caaagcatgc acaacatgcg    3660
ctaaggctaa ggcaagatgc gtccccggcc ctcttgggag cctcaagtgc gacaggtaag    3720
tcatgataat tggttcattt ttgggaatat cttgatggct tgcgtttaat cgtcgccgta    3780
ccaggcttgt cttgtaccat atacatatgt ggtgtgagtt ggtggagagg tacatatgct    3840
gacattagaa ttc                                                       3853
```

<210> SEQ ID NO 2
<211> LENGTH: 588
<212> TYPE: PRT
<213> ORGANISM: Fusarium

<400> SEQUENCE: 2

```
Met Asp Ala Val Leu Arg Gln Ser Lys Ala Met Cys Pro Phe Met Lys
  1               5                  10                  15

Thr Ala Thr Pro Ala Thr Leu Arg Ala Leu Ser Thr Ser Ser Arg Ala
             20                  25                  30

Leu Pro Ala Pro Ala Ser Pro Cys Gly Gly Thr Met Ser Lys Leu Gln
         35                  40                  45

Leu Leu Gly Gln Arg Cys Pro Val Met Ala Thr Arg Arg Leu Val Leu
     50                  55                  60

Leu Asn Ala His Ser Ser Lys Ala Thr Met Val Cys Ser Asn Pro
 65                  70                  75                  80

Thr Pro Pro Gly Ile His Ala Asn Arg Lys Ala Ser Ala Ser Pro
             85                  90                  95

Thr Ala Ser Ala Ala Ala Gly Phe Gln Ser Pro Gly Lys Phe Asp
        100                 105                 110

Tyr Glu Thr Phe Tyr Asn Thr Leu Glu Lys Lys His Lys Asp Lys
        115                 120                 125

Ser Tyr Arg Tyr Phe Asn Asn Ile Asn Arg Leu Ala Lys Glu Phe Pro
    130                 135                 140

Arg Ala His Met Ser Asp Lys Glu Asp Arg Val Thr Val Trp Cys Ala
```

-continued

```
               145                 150                 155                 160
Asn Asp Tyr Leu Gly Met Gly Arg Asn Pro His Val Leu Asn Thr Met
                   165                 170                 175
His Lys Thr Leu Glu Glu Tyr Gly Ala Gly Ala Gly Gly Thr Arg Asn
                   180                 185                 190
Ile Ser Gly His Asn Lys His Ala Val Glu Leu Glu Ala Thr Leu Ala
                   195                 200                 205
Lys Leu His Ala Lys Asp Ser Ala Leu Val Phe Ser Ser Cys Tyr Val
                   210                 215                 220
Ala Asn Asp Ala Thr Leu Ala Thr Leu Gly Ser Lys Leu Pro Glu Cys
225                 230                 235                 240
Val Ile Leu Ser Asp Ser Leu Asn His Ala Ser Met Ile Gln Gly Ile
                   245                 250                 255
Arg His Ser Gly Thr Lys Lys Ile Val Phe Lys His Asn Asp Val Gln
                   260                 265                 270
Asp Leu Glu Ala Lys Leu Ala Ser Leu Pro Leu His Val Pro Lys Ile
                   275                 280                 285
Ile Ala Phe Glu Ser Val Tyr Ser Met Cys Gly Ser Ile Gly Pro Ile
                   290                 295                 300
Glu Glu Ile Cys Asp Leu Ala Asp Lys Tyr Gly Ala Ile Thr Phe Leu
305                 310                 315                 320
Asp Glu Val His Ala Val Gly Met Tyr Gly Leu His Gly Ala Gly Val
                   325                 330                 335
Ala Glu His Leu Asp Trp Glu Ala His Ala Asn Gly Ala Leu Arg Gly
                   340                 345                 350
Thr Ile Met Asp Arg Ile Asp Ile Ile Thr Gly Thr Leu Gly Lys Ala
                   355                 360                 365
Tyr Gly Cys Val Gly Gly Tyr Ile Ala Gly Ser Ala Lys Phe Ile Asp
                   370                 375                 380
Val Ile Arg Ser Leu Ala Pro Gly Phe Ile Phe Thr Thr Ser Leu Pro
385                 390                 395                 400
Pro Ala Thr Met Ala Gly Ala Gln Thr Ser Ile Glu Tyr Gln Met Glu
                   405                 410                 415
Tyr Asp Gly Asp Arg Arg Leu Gln Gln Leu His Thr Arg Ala Val Lys
                   420                 425                 430
Glu Ala Met Asn Ala Arg Asp Ile Pro Val Ile Pro Asn Pro Ser His
                   435                 440                 445
Ile Ile Pro Val Leu Val Gly Asn Ala Glu Thr Ala Lys Ala Ala Ser
                   450                 455                 460
Asp Met Leu Leu Asn Asp Tyr Gly Ile Tyr Val Gln Ser Ile Asn Tyr
465                 470                 475                 480
Pro Thr Val Pro Val Gly Gln Glu Arg Leu Arg Ile Thr Pro Thr Pro
                   485                 490                 495
Gly His Val Lys Glu Tyr Arg Asn Gln Leu Val Glu Ala Val Asp Glu
                   500                 505                 510
Ile Trp Thr Arg Leu Asn Ile Lys Arg Thr Ser Asp Trp Ala Ala Glu
                   515                 520                 525
Gly Gly Phe Ile Gly Val Gly Glu Ser Asn Val Gln Asn Pro Leu
                   530                 535                 540
Trp Thr Asp Lys Gln Leu Asn Val Glu Gln Ala Thr Lys Glu Ile Lys
545                 550                 555                 560
Ala Thr Gly Gln Ala Ala Asn Gly Ile Thr Glu Ala Leu Leu Glu Leu
                   565                 570                 575
```

```
Glu Ile Lys Gln Ser Ser Glu Val Ala Thr Ala Ala
        580                 585

<210> SEQ ID NO 3
<211> LENGTH: 23
<212> TYPE: DNA
<213> ORGANISM: Fusarium
<220> FEATURE:
<223> OTHER INFORMATION: n = a, c, g or t

<400> SEQUENCE: 3
gtntggtgyt cnaaygayta yct                                              23

<210> SEQ ID NO 4
<211> LENGTH: 20
<212> TYPE: DNA
<213> ORGANISM: Fusarium
<220> FEATURE:
<223> OTHER INFORMATION: n = a, c, g or t

<400> SEQUENCE: 4
ccnacngcrt gnacytcrtc                                                  20

<210> SEQ ID NO 5
<211> LENGTH: 17
<212> TYPE: DNA
<213> ORGANISM: Fusarium

<400> SEQUENCE: 5
ccatacttgt cggcaag                                                     17

<210> SEQ ID NO 6
<211> LENGTH: 16
<212> TYPE: DNA
<213> ORGANISM: Fusarium

<400> SEQUENCE: 6
gaacgactac cttggc                                                      16

<210> SEQ ID NO 7
<211> LENGTH: 13
<212> TYPE: DNA
<213> ORGANISM: Fusarium

<400> SEQUENCE: 7
gatcgattta aat                                                         13

<210> SEQ ID NO 8
<211> LENGTH: 13
<212> TYPE: DNA
<213> ORGANISM: Fusarium

<400> SEQUENCE: 8
tcgaatttaa atc                                                         13

<210> SEQ ID NO 9
<211> LENGTH: 40
<212> TYPE: DNA
<213> ORGANISM: Fusarium

<400> SEQUENCE: 9
gcgaattcat atttaaatgc cgaccagcag acggccctcg                            40
```

-continued

```
<210> SEQ ID NO 10
<211> LENGTH: 30
<212> TYPE: DNA
<213> ORGANISM: Fusarium

<400> SEQUENCE: 10
gcgatatcat gatctctctg gtactcttcg                                    30

<210> SEQ ID NO 11
<211> LENGTH: 30
<212> TYPE: DNA
<213> ORGANISM: Fusarium

<400> SEQUENCE: 11
gcgatatcat cgaccagcag acggccctcg                                    30

<210> SEQ ID NO 12
<211> LENGTH: 32
<212> TYPE: DNA
<213> ORGANISM: Fusarium

<400> SEQUENCE: 12
gcgtttaaac atgatctctc tggtactctt cg                                 32
```

POLYPEPTIDES HAVING AMINOLEVULINIC ACID ACTIVITY AND NUCLEIC ACIDS ENCODING SAME

CROSS-REFERENCE TO RELATED APPLICATIONS

This application is a divisional of U.S. application Ser. No. 09/193,107 filed Nov. 16, 1998, now U.S. Pat. No. 6,033,892 which claims priority from U.S. provisional application Ser. No. 60/066,107 filed Nov. 17, 1997, which applications are fully incorporated herein by reference.

BACKGROUND OF THE INVENTION

1. Field of the Invention

The present invention relates to isolated polypeptides having 5-aminolevulinic acid synthase activity and isolated nucleic acid sequences encoding the polypeptides. The invention also relates to nucleic acid constructs, vectors, and host cells comprising the nucleic acid sequences as well as methods for producing and using the polypeptides.

2. Description of the Related Art

Heme, a chelate complex of protoporphyrin IX and iron, serves as a prosthetic group of hemoproteins. Protoporphyrin IX consists of a porphyrin ring, substituted with four methyl groups, two vinyl groups, and two propionic acid groups, which acquires an iron atom to form heme. The biosynthesis of heme from glycine and succinyl-CoA involves eight enzymatic steps. The first enzyme in the biosynthetic pathway is 5-aminolevulinic acid synthase.

The conversion of an apoprotein into a hemoprotein depends on the availability of heme provided by the heme biosynthetic pathway. The apoprotein form of the hemoprotein combines with heme to produce the active hemoprotein. The active hemoprotein acquires a conformation which makes the hemoprotein more stable than the apoprotein to proteolytic attack. If the amount of heme produced by a microorganism is less relative to the amount of the apoprotein produced, the apoprotein will accumulate and undergo proteolytic degradation lowering the yield of the active hemoprotein.

In order to overcome this problem, Jensen showed that the addition of heme or a heme-containing material to a fermentation medium led to a significant increase in the yield of a peroxidase produced by *Aspergillus oryzae* (WO 93/19195). While heme supplementation of a fermentation medium results in a significant improvement in the yield of a hemoprotein, it is non-kosher, costly, and difficult to implement on a large scale.

The overexpression of a gene in the heme biosynthetic pathway of a cell provides an alternative approach for overcoming this problem.

The cloning and sequencing of a 5-aminolevulinic acid synthase gene from *Aspergillus nidulans* (Bradshaw et al., 1993, *Current Genetics* 2233:501–507) have been disclosed.

It is an object of the present invention to provide new polypeptides having 5-aminolevulinic acid synthase activity and genes encoding same.

SUMMARY OF THE INVENTION

The present invention relates to isolated polypeptides having 5-aminolevulinic acid synthase activity selected from the group consisting of:

(a) a polypeptide having an amino acid sequence which has at least 80% identity with the amino acid sequence of SEQ ID NO:2;

(b) a polypeptide encoded by a nucleic acid sequence which hybridizes under high stringency conditions with (i) the nucleic acid sequence of SEQ ID NO:1 or (ii) its complementary strand; or a subsequence thereof of at least 100 nucleotides;

(c) an allelic variant of (a) or (b); and (d) a fragment of (a), (b) or (c), wherein the fragment has 5-aminolevulinic acid synthase activity.

The present invention also relates to isolated nucleic acid sequences encoding the polypeptides and to nucleic acid constructs, vectors, and host cells comprising the nucleic acid sequences as well as methods for producing and using the polypeptides.

BRIEF DESCRIPTION OF THE FIGURES

FIG. 1 shows the nucleic acid sequence and the deduced amino acid sequence of a Fusarium 5-aminolevulinic acid synthase (SEQ ID NOS:1 and 2, respectively).

DETAILED DESCRIPTION OF THE INVENTION

Polypeptides Having 5-Aminolevulinic Acid Synthase Activity

Figure 2:
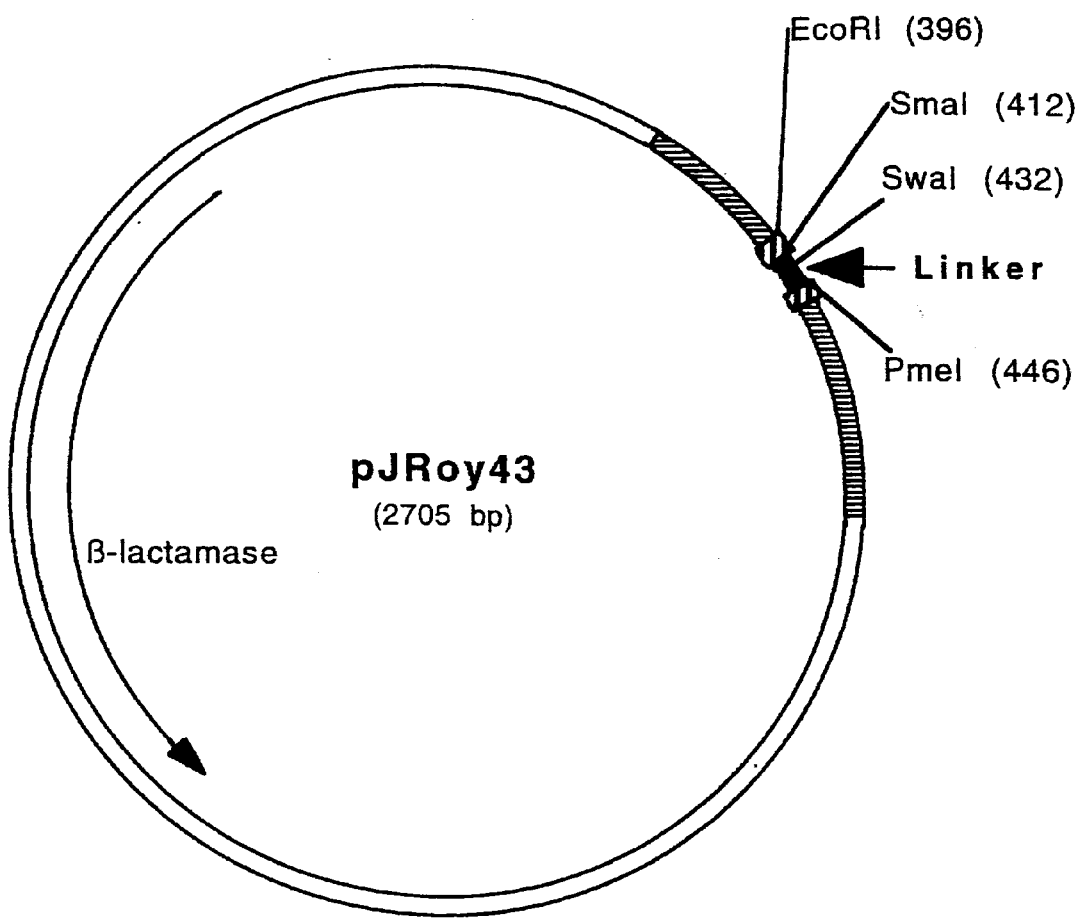
FIG. 2 shows a restriction map of pJRoy43.

The term "5-aminolevulinic acid synthase activity" is defined herein as a synthase activity which catalyzes the condensation of glycine and succinyl-CoA to form 5-aminolevulinic acid. For purposes of the present invention, 5-aminolevulinic acid synthase activity is determined according to the procedure described by Wider de Xifra et al., 1971, *Biochimica Biophysica Acta* 235: 511–517 modified by Paveto et al., 1989, *Comp. Biochem. Physiol.* 94B: 635–639 where the conversion of glycine and succinyl-CoA to 5-aminolevulinic acid is measured at pH 7.5, 25° C.

In a first embodiment, the present invention relates to isolated polypeptides having an amino acid sequence which has a degree of identity to the amino acid sequence of SEQ ID NO:2 of at least about 80%, preferably at least about 85%, more preferably at least about 90%, even more preferably at least about 95%, and even most preferably at least about 97%, which have 5-aminolevulinic acid synthase activity (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from the amino acid sequence of SEQ ID NO:2. For purposes of the present invention, the degree of identity between two amino acid sequences is determined by the Clustal method (Higgins, 1989, *CABIOS* 5: 151–153) using the LASERGENE™ MEGALIGN™ software (DNASTAR, Inc., Madison, Wis.) with an identity table and the following multiple alignment parameters: Gap penalty of 10, and gap length penalty of 10. Pairwise alignment parameters were Ktuple=1, gap penalty=3, windows=5, and diagonals=5.

Preferably, the polypeptides of the present invention comprise the amino acid sequence of SEQ ID NO:2, or an allelic variant thereof; or a fragment thereof, wherein the fragment has 5-aminolevulinic acid synthase activity. In a more preferred embodiment, the polypeptides of the present invention comprise the amino acid sequence of SEQ ID NO:2. In another preferred embodiment, the polypeptide of the present invention consists of the amino acid sequence of SEQ ID NO:2 or an allelic variant thereof; or a fragment thereof, wherein the fragment has 5-aminolevulinic acid synthase activity. In a more preferred embodiment, the polypeptide of the present invention consists of the amino acid sequence of SEQ ID NO:2.

A fragment of SEQ ID NO:2 is a polypeptide having one or more amino acids deleted from the amino and/or carboxyl terminus of this amino acid sequence. Preferably, a fragment contains at least 460 amino acid residues, more preferably at least 500 amino acid residues, and most preferably at least 540 amino acid residues.

An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The amino acid sequences of the homologous polypeptides may differ from the amino acid sequence of SEQ ID NO:2 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutarnic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/val, Ser/Gly, Tyr/Phe, Ala/Pro, Lys/Arg, Asp/Asn, Leu/Ile, Leu/Val, Ala/Glu, and Asp/Gly as well as these in reverse.

In a second embodiment, the present invention relates to isolated polypeptides having 5-aminolevulinic acid synthase activity which are encoded by nucleic acid sequences which hybridize under low stringency conditions, more preferably medium stringency conditions, even more preferably high stringency conditions, and most preferably very high stringency conditions, with a nucleic acid probe which hybridizes under the same conditions with the nucleic acid sequence of SEQ ID NO: 1 or its complementary strand; or a subsequence thereof which encodes a polypeptide fragment which has 5-aminolevulinic acid synthase activity (J. Sambrook, E. F. Fritsch, and T. Maniatus, 1989, Molecular Cloning, A Laboratory Manual, 2d edition, Cold Spring Harbor, New York). The subsequence of SEQ ID NO: 1 may be at least 100 nucleotides or preferably at least 200 nucleotides. Moreover, the subsequence may encode a polypeptide fragment which has 5-aminolevulinic acid synthase activity. The polypeptides may also be allelic variants or fragments of the polypeptides, wherein the fragments have 5-aminolevulinic acid synthase activity.

The nucleic acid sequence of SEQ ID NO: 1 or a subsequence thereof, as well as the amino acid sequence of SEQ ID NO:2 or a fragment thereof, may be used to design a nucleic acid probe to identify and clone DNA encoding polypeptides having 5-aminolevulinic acid synthase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}$p, $^{3}$H, 35S, biotin, or avidin). Such probes are encompassed by the present invention.

Thus, a genomic DNA or cDNA library prepared from such other organisms may be screened for DNA which hybridizes with the probes described above and which encodes a polypeptide having 5-aminolevulinic acid synthase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 1, the carrier material is used in a Southern blot. For purposes of the present invention, hybridization indicates that the nucleic acid sequence hybridizes to a nucleic acid probe corresponding to the nucleic acid sequence shown in SEQ ID NO: 1, its complementary strand, or a subsequence thereof, under low to very high stringency conditions. Molecules to which the nucleic acid probe hybridizes under these conditions are detected using X-ray film.

In a preferred embodiment, the nucleic acid probe is a nucleic acid sequence which encodes the polypeptide of SEQ ID NO:2, or a subsequence thereof. In another preferred embodiment, the nucleic acid probe is SEQ ID NO: 1. In another preferred embodiment, the nucleic acid probe is the nucleic acid sequence contained in plasmid pZL3-3 which is contained in Escherichia coli NRRL B-21855, wherein the nucleic acid sequence encodes the polypeptide of SEQ ID NO:2.

For long probes of at least 100 nucleotides in length, low to very high stringency conditions are defined as prehybridization and hybridization at 42° C. in 5×SSPE, 0.3% SDS, 200 μg/ml sheared and denatured salmon sperm DNA, and either 25, 35 or 50% formamide for low, medium, and high and very high stringencies, respectively, following standard Southern blotting procedures.

For long probes of at least 100 nucleotides in length, the carrier material is finally washed three times each for 15 minutes using 2×SSC, 0.2% SDS preferably at least at 45° C. (very low stringency), more preferably at least at 50° C.

(low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at 5° C. to 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third embodiment, the present invention relates to isolated polypeptides having immunochemical identity or partial immunochemical identity to the polypeptide having the amino acid sequence of SEQ ID NO:2. The immunochemical properties are determined by immunological cross-reaction identity tests by the well-known Ouchterlony double immunodiffusion procedure. Specifically, an antiserum containing polyclonal antibodies which are immunoreactive or bind to epitopes of the polypeptide having the amino acid sequence of SEQ ID NO:2 are prepared by immunizing rabbits (or other rodents) according to the procedure described by Harboe and Ingild, In N. H. Axelsen, J. Krøll, and B. Weeks, editors, *A Manual of Quantitative Immunoelectrophoresis*, Blackwell Scientific Publications, 1973, Chapter 23, or Johnstone and Thorpe, *Immunochemistry in Practice*, Blackwell Scientific Publications, 1982 (more specifically pages 27–31). A polypeptide having immunochemical identity is a polypeptide which reacts with the antiserum in an identical fashion such as total fusion of precipitates, identical precipitate morphology, and/or identical electrophoretic mobility using a specific immunochemical technique. A further explanation of immunochemical identity is described by Axelsen, Bock, and Krøll, In N. H. Axelsen, J. Krøll, and B. Weeks, editors, *A Manual of Quantitative Immunoelectrophoresis*, Blackwell Scientific Publications, 1973, Chapter 10. A polypeptide having partial immunochemical identity is a polypeptide which reacts with the antiserum in a partially identical fashion such as partial fusion of precipitates, partially identical precipitate morphology, and/or partially identical electrophoretic mobility using a specific immunochemical technique. A further explanation of partial immunochemical identity is described by Bock and Axelsen, In N. H. Axelsen, J. Krøll, and B. Weeks, editors, *A Manual of Quantitative Immunoelectrophoresis*, Blackwell Scientific Publications, 1973, Chapter 11.

The antibody may also be a monoclonal antibody. Monoclonal antibodies may be prepared and used, e.g., according to the methods of E. Harlow and D. Lane, editors, 1988, *Antibodies, A Laboratory Manual*, Cold Spring Harbor Press, Cold Spring Harbor, New York.

The polypeptides of the present invention have at least 20%, preferably at least 40%, more preferably at least 60%, even more preferably at least 80%, even more preferably at least 90%, and most preferably at least 100% of the 5-aminolevulinic acid synthase activity of SEQ ID NO:2.

A polypeptide of the present invention may be obtained from microorganisms of any genus.

A polypeptide of the present invention may be a bacterial polypeptide. For example, the polypeptide may be a gram positive bacterial polypeptide such as a Bacillus polypeptide, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis,* or *Bacillus thuringiensis* polypeptide; or a *Streptomyces* polypeptide, e.g., a *Streptomyces lividans* or *Streptomyces murinus* polypeptide; or a gram negative bacterial polypeptide, e.g., an *E. coli* or a *Pseudomonas* sp. polypeptide.

A polypeptide of the present invention may be a fungal polypeptide, and more preferably a yeast polypeptide such as a Candida, Kluyveromyces, Pichia, Saccharomyces, Schizosaccharomyces, or Yarrowia polypeptide; or more preferably a filamentous fungal polypeptide such as an Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium, or Trichoderma polypeptide.

In a preferred embodiment, the polypeptide is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* polypeptide.

In another preferred embodiment, the polypeptide is an *Aspergillus aculeatus, Aspergillus awamori, Aspergillus foetidus, Aspergillus japonicus, Aspergillus nidulans, Aspergillus niger, Aspergillus oryzae, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei,* or *Trichoderma viride* polypeptide.

In another preferred embodiment, the polypeptide is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* polypeptide.

In a more preferred embodiment, the *Fusarium venenatum* cell is *Fusarium venenatum* A3/5, which was originally deposited as *Fusarium graminearum* ATCC 20334 and recently reclassified as *Fusarium venenatum* by Yoder and Christianson, 1998, *Fungal Genetics and Biology* 23: 62–80 and O'Donnell et al., 1998, *Fungal Genetics and Biology* 23: 57–67; as well as taxonomic equivalents of Fusarium venenatum regardless of the species name by which they are currently known. In another preferred embodiment, the *Fusarium venenatum* cell is a morphological mutant of *Fusarium venenatum* A3/5 or *Fusarium venenatum* ATCC 20334, as disclosed in WO 97/26330.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents. For example, taxonomic equivalents of Fusarium are defined by D. L. Hawksworth, P. M. Kirk, B. C. Sutton, and D. N. Pegler (editors), 1995, In Ainsworth & Bisby's *Dictionary of the Fungi*, Eighth Edition, CAB International, University Press, Cambridge, England, pp. 173–174.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

As defined herein, an "isolated" polypeptide is a polypeptide which is essentially free of other non-5-aminolevulinic acid synthase polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

Polypeptides encoded by nucleic acid sequences of the present invention also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Nucleic Acid Sequences

The present invention also relates to isolated nucleic acid sequences which encode a polypeptide of the present invention. In a preferred embodiment, the nucleic acid sequence is set forth in SEQ ID NO:1. In another more preferred embodiment, the nucleic acid sequence is the sequence contained in plasmid pZL3-3 which is contained in *Escherichia coli* NRRL B-21855. The present invention also encompasses nucleic acid sequences which encode a polypeptide having the amino acid sequence of SEQ ID NO:2, which differ from SEQ ID NO:1 by virtue of the degeneracy of the genetic code. The present invention also relates to subsequences of SEQ ID NO: 1 which encode fragments of SEQ ID NO:2 which have 5-aminolevulinic acid synthase activity.

A subsequence of SEQ ID NO:1 is a nucleic acid sequence encompassed by SEQ ID NO:1 except that one or more nucleotides from the 5' and/or 3' end have been deleted. Preferably, a subsequence contains at least 1380 nucleotides, more preferably at least 1500 nucleotides, and most preferably at least 1620 nucleotides.

The present invention also relates to mutant nucleic acid sequences comprising at least one mutation in the nucleic acid sequence of SEQ ID NO:1, in which the mutant nucleic acid sequence encodes a polypeptide having the amino acid sequence of SEQ ID NO:2.

The techniques used to isolate or clone a nucleic acid sequence encoding a polypeptide are known in the art and include isolation from genomic DNA, preparation from cDNA, or a combination thereof The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, PCR: *A Guide to Methods and Application*, Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of Fusarium, or another or related organism and thus, for example, may be an allelic or species variant of the polypeptide encoding region of the nucleic acid sequence.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by.standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The present invention also relates to nucleic acid sequences which have a degree of homology to the nucleic acid sequence of SEQ ID NO:1 of at least about 80%, preferably about 85%, more preferably about 90%, even more preferably about 95%, and most preferably about 97% homology, which encode an active polypeptide. For purposes of the present invention, the degree of homology between two nucleic acid sequences is determined by the Wilbur-Lipman method (Wilbur and Lipman, 1983, *Proceedings of the National Academy of Science* USA 80: 726–730) using the LASERGENE™ MEGALIGN™ software (DNASTAR, Inc., Madison, Wis.) with an identity table and the following multiple alignment parameters: Ktuple=3, gap penalty=3, and windows=20.

Modification of a nucleic acid sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source. For example, it may be of interest to synthesize variants of the polypeptide where the variants differ in specific activity, thermostability, pH optimum, or the like using, e.g., site-directed mutagenesis. The analogous sequence may be constructed on the basis of the nucleic acid sequence presented as the polypeptide encoding part of SEQ ID NO:1, e.g., a subsequence thereof, and/or by introduction of nucleotide substitutions which do not give rise to another amino acid sequence of the polypeptide encoded by the nucleic acid sequence, but which corresponds to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081–1085). In the latter technique, mutations are introduced at every positively charged residue in the molecule, and the resultant mutant molecules are tested for 5-aminolevulinic acid synthase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306–312; Smith et al, 1992, *Journal of Molecular Biology* 224: 899–904; Wlodaver et al., 1992, *FEBS Letters* 309: 59–64).

The present invention also relates to isolated nucleic acid sequences encoding a polypeptide of the present invention, which hybridize under low stringency conditions, more preferably medium stringency conditions, even more preferably high stringency conditions, and most preferably very high stringency conditions, with a nucleic acid probe which hybridizes under the same conditions with the nucleic acid sequence of SEQ ID NO:1 or its complementary strand; or allelic variants and subsequences thereof (Sambrook et al., 1989, supra), as defined herein.

The present invention also relates to isolated nucleic acid sequences produced by (a) hybridizing a DNA with the sequence of SEQ ID NO:I, or its complementary strand, or a subsequence thereof which encodes a polypeptide fragment which has 5-aminolevulinic acid synthase activity, under low, medium, high, or very high stringency conditions; and (b) isolating the nucleic acid sequence.

Methods for Producing Mutant Nucleic Acid Sequences

The present invention further relates to methods for producing a mutant nucleic acid sequence, comprising introducing at least one mutation into the nucleic acid sequence of SEQ ID NO:1 or a subsequence thereof, wherein the mutant nucleic acid sequence encodes a polypeptide having an amino acid sequence of SEQ ID NO:2 or a fragment thereof which has 5-aminolevulinic acid synthase activity.

The introduction of a mutation into the nucleic acid sequence to switch one nucleotide for another nucleotide may be accomplished by site-directed mutagenesis using any of the methods known in the art. Particularly useful is the procedure which utilizes a supercoiled, double stranded DNA vector with an insert of interest and two synthetic primers containing the desired mutation. The nucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used.

Nucleic Acid Constructs

The present invention also relates to nucleic acid constructs comprising a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion. "Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the MRNA. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The term "control sequences" is defined herein to include all components which are necessary or advantageous for the expression of a polypeptide of the present invention. Each control sequence may be native or foreign to the nucleic acid sequence encoding the polypeptide. Such control sequences include, but are not limited to, a leader, a polyadenylation sequence, a propeptide sequence, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the expression of a polypeptide.

The control sequence may be an appropriate promoter sequence, a nucleic acid sequence which is recognized by a host cell for expression of the nucleic acid sequence. The promoter sequence contains transcriptional control sequences which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, the *Streptomyces coelicolor* agarase gene (dagA), the *Bacillus subtilis* levansucrase gene (sacB), the *Bacillus licheniformis* alpha-amylase gene (amyL), the *Bacillus stearothermophilus* maltogenic amylase gene (amyM), the *Bacillus amyloliquefaciens* alpha-amylase gene (amyQ), the *Bacillus licheniformis* penicillinase gene (penP), the *Bacillus subtilis* xylA and xylB genes, and the prokaryotic beta-lactamase gene (Villa-Kamaroff et al., 1978, *Proceedings of the National Academy of Sciences USA* 75: 3727–3731), as well as the tac promoter (DeBoer et al., 1983, *Proceedings of the National Academy of Sciences USA* 80: 21–25). Further promoters are described in "Useful proteins from recombinant bacteria" in *Scientific American*, 1980, 242: 74–94; and in Sambrook et al., 1989, supra.

Examples of suitable promoters for directing the transcription of the nucleic acid constructs of the present invention in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (WO 96/00787), NA2-tpi (a hybrid of the promoters from the genes encoding *Aspergillus niger* neutral alpha-amylase and *Aspergillus oryzae* triose phosphate isomerase), and mutant, truncated, and hybrid promoters thereof In a yeast host, useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, *Yeast* 8: 423–488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes encoding *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes encoding *Saccharomyces cerevisiae* enolase, *Saccharomyces cerevisiae* cytochrome C (CYC1), or *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

Preferred leaders for filamentous fungal host cells are obtained from the genes encoding *Aspergillus oryzae* TAKA amylase and *Aspergillus nidulans* triose phosphate isomerase.

Suitable leaders for yeast host cells are obtained from the *Saccharomyces cerevisiae* enolase (ENO-1) gene, the *Saccharomyces cerevisiae* 3-phosphoglycerate kinase gene, the *Saccharomyces cerevisiae* alpha-factor, and the *Saccharomyces cerevisiae* alcohol dehydrogenase/glyceraldehyde-3-phosphate dehydrogenase genes (ADH2/GAP).

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes encoding *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983–5990.

The control sequence may also be a signal peptide coding region, which codes for an amino acid sequence linked to the amino terminus of the polypeptide which can direct the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide. However, any signal peptide coding region which directs the expressed polypeptide into the secretory pathway of a host cell of choice may be used in the present invention.

An effective signal peptide coding region for bacterial host cells is the signal peptide coding region obtained from the maltogenic amylase gene from Bacillus NCIB 11837, the *Bacillus stearothermophilus* alpha-amylase gene, the *Bacillus licheniformis* subtilisin gene, the *Bacillus licheniformis* beta-lactamase gene, the *Bacillus stearothermophilus* neutral proteases genes (nprT, nprS, nprM), or the *Bacillus subtilis* prsA gene. Further signal peptides are described by Simonen and Palva, 1993, *Microbiological Reviews* 57: 109–137.

An effective signal peptide coding region for filamentous fungal host cells is the signal peptide coding region obtained from the *Aspergillus oryzae* TAKA amylase gene, *Aspergillus niger* neutral amylase gene, *Aspergillus niger* glucoamylase gene, *Rhizomucor miehei* aspartic proteinase gene, *Humicola insolens* cellulase gene, or *Humicola lanuginosa* lipase gene.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the Bacillus subtilis alkaline protease gene (aprE), the *Bacillus subtilis* neutral protease gene (nprT), the Saccharomyces cerevisiae alpha-factor gene, the *Rhizomucor miehei* aspartic proteinase gene, or the *Myceliophthora thermophila* laccase gene (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, *Aspergillus niger* glucoamylase promoter, and the *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

The present invention also relates to nucleic acid constructs for altering the expression of an endogenous gene encoding a polypeptide of the present invention. The constructs may contain the minimal number of components necessary for altering expression of the endogenous gene. In one embodiment, the nucleic acid constructs preferably contain (a) a targeting sequence, (b) a regulatory sequence, (c) an exon, and (d) a splice-donor site. Upon introduction of the nucleic acid construct into a cell, the construct inserts by homologous recombination into the cellular genome at the endogenous gene site. The targeting sequence directs the integration of elements (a)–(d) into the endogenous gene such that elements (b)–(d) are operably linked to the endogenous gene. In another embodiment, the nucleic acid constructs contain (a) a targeting sequence, (b) a regulatory sequence, (c) an exon, (d) a splice-donor site, (e) an intron, and (f) a splice-acceptor site, wherein the targeting sequence directs the integration of elements (a)–(f) such that elements (b)–(f) are operably linked to the endogenous gene. However, the constructs may contain additional components such as a selectable marker.

In both embodiments, the introduction of these components results in production of a new transcription unit in which expression of the endogenous gene is altered. In essence, the new transcription unit is a fusion product of the sequences introduced by the targeting constructs and the endogenous gene. In one embodiment in which the endogenous gene is altered, the gene is activated. In this embodiment, homologous recombination is used to replace, disrupt, or disable the regulatory region normally associated with the endogenous gene of a parent cell through the insertion of a regulatory sequence which causes the gene to be expressed at higher levels than evident in the corresponding parent cell. The activated gene can be further amplified by the inclusion of an amplifiable selectable marker gene in the construct using methods well known in the art (see, for example, U.S. Pat. No. 5,641,670). In another embodiment in which the endogenous gene is altered, expression of the gene is reduced.

The targeting sequence can be within the endogenous gene, immediately adjacent to the gene, within an upstream gene, or upstream of and at a distance from the endogenous gene. One or more targeting sequences can be used. For example, a circular plasmid or DNA fragment preferably employs a single targeting sequence, while a linear plasmid or DNA fragment preferably employs two targeting sequences.

The regulatory sequence of the construct can be comprised of one or more promoters, enhancers, scaffold-attachment regions or matrix attachment sites, negative regulatory elements, transcription binding sites, or combinations of these sequences.

The constructs further contain one or more exons of the endogenous gene. An exon is defined as a DNA sequence which is copied into RNA and is present in a mature mRNA molecule such that the exon sequence is in-frame with the coding region of the endogenous gene. The exons can, optionally, contain DNA which encodes one or more amino acids and/or partially encodes an amino acid. Alternatively, the exon contains DNA which corresponds to a 5' non-encoding region. Where the exogenous exon or exons encode one or more amino acids and/or a portion of an amino acid, the nucleic acid construct is designed such that, upon transcription and splicing, the reading frame is in-frame with the coding region of the endogenous gene so that the appropriate reading frame of the portion of the mRNA derived from the second exon is unchanged.

The splice-donor site of the constructs directs the splicing of one exon to another exon. Typically, the first exon lies 5' of the second exon, and the splice-donor site overlapping and flanking the first exon on its 3' side recognizes a splice-acceptor site flanking the second exon on the 5' side of the second exon. A splice-acceptor site, like a splice-donor site, is a sequence which directs the splicing of one exon to another exon. Acting in conjunction with a splice-donor site, the splicing apparatus uses a splice-acceptor site to effect the removal of an intron.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. A selectable marker for use in a filamentous fungal host cell may be selected from the group including, but not limited to, amdA (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthanilate synthase), as well as equivalents from other species. Preferred for use in an Aspergillus cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell genome or autonomous replication of the vector in the cell independent of the genome of the cell.

For integration into the host cell genome, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMB1 permitting replication in Bacillus. Examples of origins of replication for use in a yeast host cell are the 2 micron origin of replication, ARS 1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75:1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular cells are bacterial cells such as gram positive bacteria including, but not limited to, a Bacillus cell, e.g., *Bacillus alkalophilus, Bacillus amyloliquefaciens,*

*Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis,* and *Bacillus thuringiensis*; or a Streptomyces cell, e.g., *Streptomyces lividans* or *Streptomyces murinus*, or gram negative bacteria such as *E. coli* and Pseudomonas sp. In a preferred embodiment, the bacterial host cell is a *Bacillus lentus, Bacillus licheniformis, Bacillus stearothermophilus* or *Bacillus subtilis* cell. In another preferred embodiment, the Bacillus cell is an alkalophilic Bacillus.

The introduction of a vector into a bacterial host cell may, for instance, be effected by protoplast transformation (see, e.g, Chang and Cohen, 1979, *Molecular General Genetics* 168: 111–115), using competent cells (see, e.g., Young and Spizizin, 1961, *Journal of Bacteriology* 81: 823–829, or Dubnau and Davidoff-Abelson, 1971, Journal of Molecular Biology 56: 209–221), electroporation (see, e.g., Shigekawa and Dower, 1988, Biotechniques is 6: 742–751), or conjugation (see, e.g, Koehler and Thorne, 1987, *Journal of Bacteriology* 169: 5771–5278).

The host cell may be a eukaryote, such as a mammalian cell, an insect cell, a plant cell or a fungal cell.

In a preferred embodiment, the host cell is a fungal cell. "Fungi" as used herein includes the phyla Ascomycota, Basidiomycota, Chytridiomycota, and Zygomycota (as defined by Hawksworth et al., In, Ainsworth and Bisby's *Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred embodiment, the yeast host cell is a Candida, Hansenula, Klyveromyces, Pichia, Saccharomyces, Schizosaccharomyces, or Yarrowia cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Tolypocladium, or Trichoderma.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In an even most preferred embodiment, the filamentous fungal parent cell is a *Fusarium venenatum* (Nirenberg sp. nov.) cell. In another most preferred embodiment, the filamentous fungal host cell is a *Humicola insolens* or *Humicola lanuginosa* cell. In another most preferred embodiment, the filamentous fungal host cell is a *Myceliophthora miehei* cell. In another most preferred embodiment, the filamentous fungal host cell is a *Myceliophthora thermophila* cell. In another most preferred embodiment, the filamentous fungal host cell is a *Neurospora crassa* cell. In another most preferred embodiment, the filamentous fungal host cell is a *Penicillium purpurogenum* cell. In another most preferred embodiment, the filamentous fungal host cell is a *Thielavia terrestris* cell. In another most preferred embodiment, the Trichoderma cell is a *Trichoderma harzianum, Trichoderma koningii, Trichoderma longibrachiatum, Trichoderma reesei* or *Trichoderma viride* cell.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, *Proceedings of the National Academy of Sciences USA* 81: 1470–1474. Suitable methods for transforming Fusarium species are described by Malardier et al., 1989, *Gene* 78: 147–156 and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182–187, Academic Press, Inc., New York; Ito et al., 1983, *Journal of Bacteriology* 153: 163; and Hinnen et al., 1978, *Proceedings of the National Academy of Sciences* USA 75: 1920.

Methods of Production

The present invention also relates to methods for producing a polypeptide of the present invention comprising (a) cultivating a strain, which in its wild-type form is capable of producing the polypeptide, to produce a supernatant comprising the polypeptide; and (b) recovering the polypeptide. Preferably, the strain is of the genus Fusarium, and more preferably *Fusarium venenatum*.

The present invention also relates to methods for producing a polypeptide of the present invention comprising (a) cultivating a host cell under conditions conducive for production of the polypeptide; and (b) recovering the polypeptide.

The present invention also relates to methods for producing a polypeptide of the present invention comprising (a) cultivating a host cell under conditions conducive for production of the polypeptide, wherein the host cell comprises a mutant nucleic acid sequence of SEQ ID NO:1 having at least one mutation in the nucleic acid sequence of SEQ ID NO:1, wherein the mutant nucleic acid sequence encodes a polypeptide having an amino acid sequence of SEQ ID NO:2, and (b) recovering the polypeptide.

The present invention further relates to methods for producing a polypeptide of the present invention comprising (a) cultivating a homologously recombinant cell, having incorporated therein a new transcription unit comprising a regulatory sequence, an exon, and/or a splice donor site operably linked to a second exon of an endogenous nucleic acid sequence encoding the polypeptide, under conditions conducive for production of the polypeptide; and (b) recovering the polypeptide. The methods are based on the use of gene activation technology, for example, as described in U.S. Pat. No. 5,641,670. Gene activation technology is based on activating a gene which is normally unexpressed in a cell or increasing expression of a gene which is expressed at very low levels in a cell. Gene activation technology includes methods of inserting an exogenous DNA construct containing a regulatory sequence, an exon, and/or a splice donor site into the genomic DNA of a cell in such a manner that the insertion results in the production of a new transcription unit in which the regulatory sequence, the exon, and/or the splice donor site are operably linked to and activate expression of the endogenous gene.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection); If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide. Procedures for determining 5-aminolevulinic acid synthase activity are known in the art. As described earlier, 5-aminolevulinic acid synthase activity is determined according to the procedure described by Wider de Xifra et al., 1971, supra, modified by Paveto et al., 1989, supra.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Uses

The present invention is also directed to methods of using the polypeptides having 5-aminolevulinic acid synthase activity.

The polypeptides of the present invention may be used to increase the yield of a hemoprotein produced by a host cell, where 5-aminolevulinic acid synthase activity is a rate-limiting step in the production of heme in the host cell, by overexpressing the nucleic acid sequence encoding the polypeptide having 5-aminolevulinic acid synthase activity in the host cell. The method comprises: (a) introducing into the host cell, which is capable of producing the hemoprotein, one or more copies of the nucleic acid sequence encoding the polypeptide having 5-aminolevulinic acid synthase activity, wherein the nucleic acid sequence is operably linked to regulatory regions capable of directing the expression of the polypeptide; (b) cultivating the cell in a nutrient medium suitable for production of the hemoprotein and the polypeptide; and (c) recovering the hemoprotein from the nutrient medium of the cell (see WO 97/47746).

The present invention may also be used for the production of heterologous polypeptides. The method comprises (a) introducing into a respiratory-efective mutant of a cell a nucleic acid construct comprising a first nucleic acid sequence encoding a polypeptide of the present invention and a second nucleic acid sequence, wherein the first nucleic acid sequence upon expression complements the respiratory defect and the second nucleic acid sequence encodes a heterologous polypeptide; (b) cultivating the cell containing the first and second nucleic acid sequences in a culture medium under aerobic conditions suitable for expression of the first and second nucleic acid sequences; and (c) recovering the heterologous polypeptide (see WO 98/41640).

The present invention is further described by the following examples which should not be construed as limiting the scope of the invention.

EXAMPLES

Media

50× Vogels medium was composed per liter of 150 g of sodium citrate, 250 g of $KH_2PO_4$, 10 g of $MgSO_4.7H_2O$, 10 g of $CaCl_2.2H_2O$, 2.5 ml of biotin stock solution, and 5.0 ml of trace metals solution.

Trace metals solution was composed per liter of 14.3 g of $ZnSO_4.7H_2O$, 2.5 g of $CuSO_4.5H_2O$, 0.5 g of $NiCl_2$, 13.8 g of $FeSO_4$, 8.5 g of $MnSO_4$, and 3.0 g of citric acid.

RA sporulation medium was composed per liter of 50 g of succinic acid, 12.1 g of $NaNO_3$, 1 g of glucose, 20 ml of 50× Vogels, and 0.5 ml of a 10 mg/ml $NaMoO_4$ stock solution, pH to 6.0.

YEG medium was composed per liter of 5 g of yeast extract and 20 g of glucose.

YEPG medium was composed per liter of 10 g of yeast extract, 20 g of peptone, and 20 g of glucose.

STC was composed of 0.8 M sorbitol, 25 mM Tris pH 8, 25 mM $CaCl_2$.

SPTC was composed of 40% PEG 4000, 0.8 M sorbitol, 25 mM Tris pH 8, 25 mM $CaCl_2$.

M400 medium (pH 6.0) was composed per liter of 50 g of maltodextrin, 2 g of $MgSO_4.7H_2O$, 2 g of $KH_2PO_4$, 4 g of citric acid, 8 g of yeast extract, 2 g of urea, 0.5 ml of trace metals solution, and 0.5 g of $CaCl_2$.

COVE trace metals solution was composed per liter of 0.04 g of NaB$_4$O$_7$.10H$_2$O, 0.4 g of CuSO$_4$.5H$_2$O, 1.2 g of FeSO$_4$.7H$_2$O, 0.7 g of MnSO$_4$.H$_2$O, 0.8 g of Na$_2$MoO$_2$.2H$_2$O, and 10 g of ZnSO$_4$.7H$_2$O.

Minimal medium overlay (pH 6.5) was composed per liter of 6.0 g of NaNO$_3$, 0.52 g of KCl, 1.52 g of KH2PO$_4$, 1 ml of COVE trace metals solution, 20 ml of 50% glucose, 2.5 ml of 20% MgSO$_4$.7H$_2$O, 20 ml of biotin stock solution, and 20 g of low melting point agarose.

Biotin stock solution was composed of 5 mg of biotin in 100 ml of 50% ethanol.

Minimal medium plates (pH 6.5) were composed of 6.0 g of NaNO$_3$, 0.52 g of KCl, 1.52 g of KH$_2$PO$_4$, 1.0 ml of COVE trace metals solution, 20 g of Nobel Agar (Difco), 20 ml of 50% glucose, 20 ml of methionine (50 g/l), 20 ml of biotin (200 mg/l), 2.5 ml of 20% MgSO$_4$.7H$_2$O, and 1.0 ml of mg/ml streptomycin.

Example 1

Fusarium graminearum strain ATCC 20334 genomic DNA extraction

*Fusarium graminearum* (=*Fusarium venenatum*) strain ATCC 20334 was grown in 25 ml of 0.5% yeast extract-2% glucose (YEG) medium for 72 hours at 30° C. and 250 rpm. Mycelia were then collected by filtration through Miracloth (Calbiochem, La Jolla, Calif.) and washed once with 25 ml of 10 mM Tris-1 mM EDTA (TE) buffer. Excess buffer was drained from the mycelia which were subsequently frozen in liquid nitrogen. The frozen mycelia were ground to a fine powder in an electric coffee grinder, and the powder was added to 20 ml of TE buffer and 5 ml of 20% w/v sodium dodecylsulfate (SDS) in a disposable plastic centrifuge tube. The mixture was gently inverted several times to insure mixing, and extracted twice with an equal volume of phenol:chloroform:isoamyl alcohol (25:24:1 v/v/v). Sodium acetate (3 M solution) was added to a final concentration of 0.3 M followed by addition of 2.5 volumes of ice cold ethanol to precipitate the nucleic acids. The nucleic acids were then pelleted by 25 centrifuging the tube at 15,000×g for 30 minutes. The pellet was allowed to air dry for 30 minutes before resuspension in 0.5 ml of TE buffer. DNase-free ribonuclease A was added to a concentration of 100 mg/ml and the mixture was incubated at 37° C. for 30 minutes. Proteinase K was then added at a concentration of 200 mg/ml and the mixture was incubated an additional hour at 37° C. Finally, the mixture was extracted twice with phenol:chloroform:isoamyl alcohol (25:24:1 v/v/v) before precipitating the DNA with sodium acetate and ethanol as described earlier. The DNA pellet was dried under vacuum, resuspended in TE buffer, and stored at 4° C. until further use.

Example 2

Construction of plasmid pGAGa5

Plasmid pGAGa5 was constructed by ligation of PCR fragments from an amplification reaction containing Fusarium strain ATCC 20334 genornic DNA. The amplification reaction contained the following components: 50 ng of genomic DNA, 100 µM each of dATP, dCTP, dGTP, and dTTP (Boehringer Mannheim, Indianapolis, Ind.), 50 pmoles of primers hemADeg5' 5'-GTITGGTGYTCIAAYGAYTAYCT-3' (SEQ ID NO:3) and hemADeg3' 5'-CCNACNGCRTGNACYTCRTC-3' (SEQ ID NO:4), 2 units of Taq DNA polymerase (Perkin-Elmer Corp., Branchburg, N.J.), and IX Taq DNA polymerase buffer (Perkin-Elmer Corp., Branchburg, N.J.). The reaction was incubated in a Perkin-Elmer Thermal Cycler (Perkin-Elmer Corp., Branchburg, N.J.) programmed for 30 cycles each at 95° C. for 1 minute, 53° C. for 1 minute, and 72° C. for 90 seconds. The 450 bp PCR product was isolated by excision after electrophoresis using a 1.1% low melting temperature agarose gel (FMC, Rockland, Me.) with 40 mM Tris-acetate-1 mM disodium EDTA (TAE) buffer, and subcloned into the pCRII vector (Invitrogen, San Diego, Calif.) according to the manufacturer's instructions to produce pGAGa5.

Example 3

Fusarium DNA Libraries and Identification of 5-Aminolevulinic Acid Synthase (hemA) Clones Fusarzum strain ATCC 20334 genomic DNA libraries were constructed using the bacteriophage cloning vector λZipLox (Life Technologies, Gaithersburg, Md.) according to the manufacturer's instructions using *E. coli* Y1090ZL cells as a host for plating and purification of recombinant bacteriophage and *E. coli* DH10Bzip for excision of individual pZL1-hemA clones. Total cellular DNA prepared as described in Example 1 was partially digested with Tsp509I and size-fractionated on a 1% agarose gel with 50 mM Tris-50 mM borate-1 mM disodium EDTA (TBE) buffer. DNA fragments migrating in the size range 4–7 kb were excised and eluted from the gel using Prep-a-Gene reagents (BioRad Laboratories, Hercules, Calif.). The eluted DNA fragments were ligated with EcoRI-cleaved and dephosphorylated λZipLox vector arms, and the ligation mixtures were packaged using commercial packaging extracts (Stratagene, La Jolla, Calif.). The packaged DNA libraries were plated and amplified in *E. coli* Y1090ZL cells. The unamplified genomic library contained 1×10$^6$ pfu/ml.

Bacteriophage DNA from 7×10$^4$ plaques was transferred to duplicate circular Nytran Plus membranes (Schleicher & Schuell, Keene, N.H.) and probed with a digoxigenin (DIG)-labeled probe which was prepared by PCR amplification of Fusarium strain ATCC 20334 genomic DNA from plasmid pGAGa5 described in Example 3. The amplification reaction contained the following components: 1× DIG probe synthesis mix (Boehringer Mannheim, Indianapolis, Ind.), 50 pmoles of primer hemA5' 38 5'-CCATACTTGTCGGCAAG-3' (SEQ ID NO:5) and primer hemA3'423 5'-GAACGACTACCTTGGC-3' (SEQ ID NO:6), 2 units of Taq DNA polymerase, and 1× Taq DNA polymerase buffer. The reaction was incubated in a Perkin-Elmer Thermal Cycler programmed for 30 cycles each at 95° C. for 1 minute, 55° C. for 1 minute, and 72° C. for 2 minutes. Denatured probe was added to the hybridization buffer at a concentration of 2 ng/ml and incubated overnight with prehybridized membranes. Prehybridization and hybridization was conducted at 42° C. in 5×SSC–0.1% sarkosyl, 0.02% SDS, 1% Genius blocking agent (Boehringer Mannheim, Indianapolis, Ind.), and 30% formamide. Membranes were washed twice in 5×SSC–0.1% SDS followed by two washes in 2×SSC–0.1% SDS. Each wash was performed for 15 minutes at room temperature. The washed membrane was exposed to Kodak X-OMAT AR film for approximately 2 hours at room temperature followed by development using a Konica QX-70 automatic film processor according to the manufacturer's instructions. Primary plaques were purified and screened a second time. Three clones were identified and excised into pZL derivatives according to the manufacturer's instructions (Bethesda Research Laboratories, Inc., Gaithersburg, Md.). The pZL derivatives were designated pZL1-3, pZL3-3, and pZL12-1, and were found to contain a 3.8 kb region.

Example 4

Characterization of Fusarium 5-Aminolevulinic Acid Synthase (hemA) Gene pZL3-3 described in Example 3 was subjected to DNA sequencing according to the following procedure. DNA sequencing was performed with an Applied Biosystems Model 373A Automated DNA Sequencer (Applied Biosystems, Inc., Foster City, Calif.) on both strands using the primer walking technique with dye-terminator chemistry (Giesecke et al., 1992, *Journal of Virol. Methods* 38:47–60) using the M13 reverse (-48) and M13 forward (-20) primers (New England Biolabs, Beverly, Md.) and primers unique to the DNA being sequenced.

The nucleotide sequence of the cloned gene revealed an open reading frame of 1922 nucleotides as shown FIG. 1 (SEQ ID NO: 1) punctuated by two short putative introns. The nucleotide sequence encodes a predicted protein of 588 amino acids with a molecular weight 65 kDa.

The deduced amino acid sequence of the Fusarium strain ATCC 20334 gene product is shown in FIG. 1 (SEQ ID NO:2). Overall, the deduced amino acid sequence shares 73% identity with the *Aspergillus nidulans* hemA gene (Bradshaw et al., 1993, supra), and 57% identity with the *Saccharomyces cerevisiae* HEM1 gene (Urban-Grimal, 1986, *European Journal of Biochemistry* 156:511–519), which were determined by the Clustal method (Higgins, 1989, *CABIOS* 5: 151–153) using the LASERGENE™ MEGALIGN™ software (DNASTAR, Inc., Madison, Wis.) with an identity table and the following multiple alignment parameters: Gap penalty of 10, and gap length penalty of 10. Pairwise alignment parameters were Ktuple=1, gap penalty=3, windows=5, and diagonals=5.

Example 5

Construction of pΔHemA

Plasmid pΔHemA was constructed to contain a hemAΔ::amdS allele.

Plasmid pJRoy47 was first constructed to contain the *Aspergillus nidulans* amdS gene flanked by 224 bp direct repeats designed to facilitate recombination and removal of the amds marker. pNEB193 (New England Biolabs, Beverly, Mass.) was digested with BamHI and SalI and gel purified using the Qiaquick Gel Extraction Kit (Qiagen, Inc., Chatsworth, Calif.). Two oligonucleotides, Bam/Swa/Sal linker 3 and Bam/Swa/Sal linker 4 (shown below), were resuspended in water to a concentration of 50 pmol per µl, mixed, heated to 50° C. for 10 minutes, and then slow cooled.

Bam/Swa/Sal linker 3: 5'-GATCGATTTAAAT-3' (SEQ ID NO:7)

Bam/Swa/Sal linker 4: 5'-TCGAATTTAAATC-3' (SEQ ID NO:8)

This oligonucleotide was ligated into the BamHI and SalI restricted pNEB193 described above to produce plasmid pJRoy43 (FIG. 2).

In order to produce the repeat fragments, two PCR reactions were carried out with the primer pairs shown below.

Pair1:
Repeat Oligo 1:
5'-GCGAATTCATATTTAAATGCCGACCAGCAGAC GGCCCTCG-3' (SEQ ID NO:9)

Repeat Oligo 2:
5'-GCGATATCATGATCTCTCTGGTACTCTTCG-3' (SEQ ID NO:10)

Pair2:
Repeat Oligo 3:
5'-GCGATATCATCGACCAGCAGACGGCCCTCG-3' (SEQ ID NO:11)

Repeat Oligo 4:
5'-GCGTTTAAACATGATCTCTCTGGTACTCTTCG-3' (SEQ ID NO:12)

The amplification reactions (50 µl) contained the following components: 50 ng of pJaL493 (WO 98/41640), 50 pmol of Repeat Oligo 1 and 50 pmol of Repeat Oligo 2, or 50 pmol of Repeat Oligo 3 and 50 pmol of Repeat Oligo 4, 5 µl of 2.5 mM DATP, dCTP, dGTP, and dTTP, 1×Taq polymerase buffer (Perkin-Elmer Corp., Branchburg, N.J.), and 5 Units of Taq polymerase (Perkin-Elmer Corp., Branchburg, N.J.). The reaction was incubated in a Perkin-Elmer Model 480 Thermal Cycler programmed as follows: Cycle 1 at 95° C. for 5 minutes, 55° C. for 2 minutes, and 72° C. for 5 minutes; Cycle 2–30 each at 95° C. for 1 minute; 55° C. for 1 minute, and 72° C. for 1 minute; and a Soak cycle at 4° C. The resulting 224 bp fragments were run on a 1% agarose gel in TAE buffer and gel purified using the Qiaquick Gel Extraction Kit. Then these fragments were digested with EcoRV and EcoRI, ligated to one another and again gel purified using the Qiaquick Gel Extraction Kit.

Figure 3:
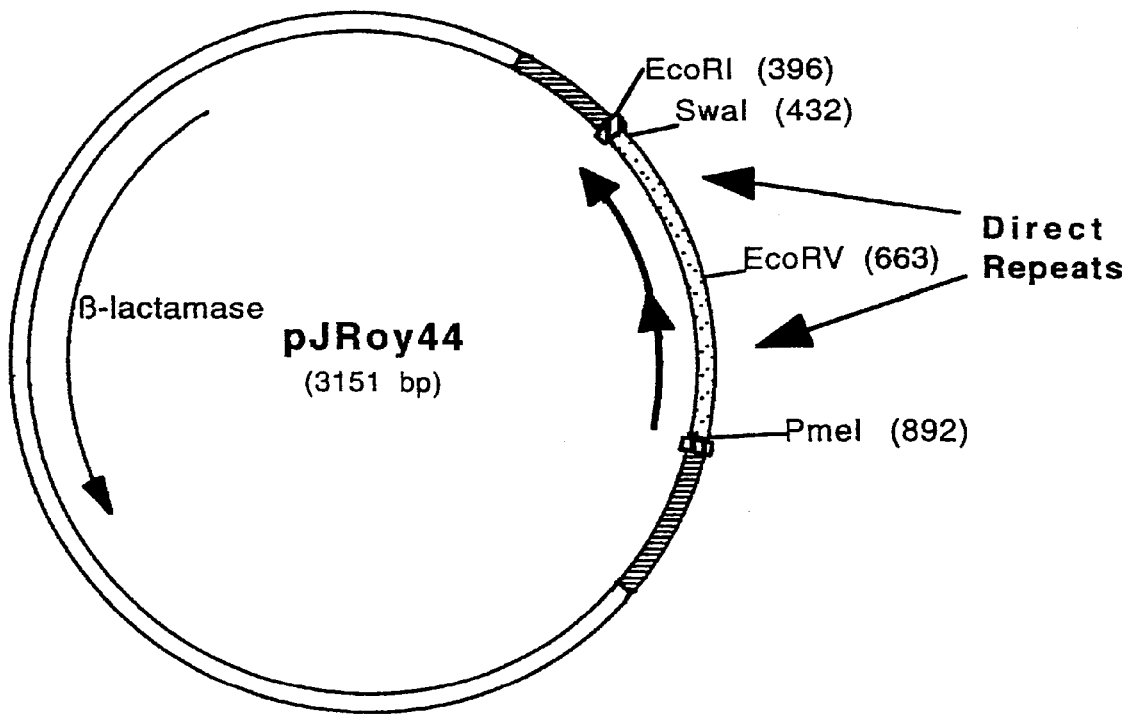
FIG. 3 shows a restriction map of pJRoy44.

Plasmid pJRoy43 and the repeat containing fragment were both digested with SwaI and PmeI and ligated together to produce pJRoy44 (FIG. 3).

Figure 4:
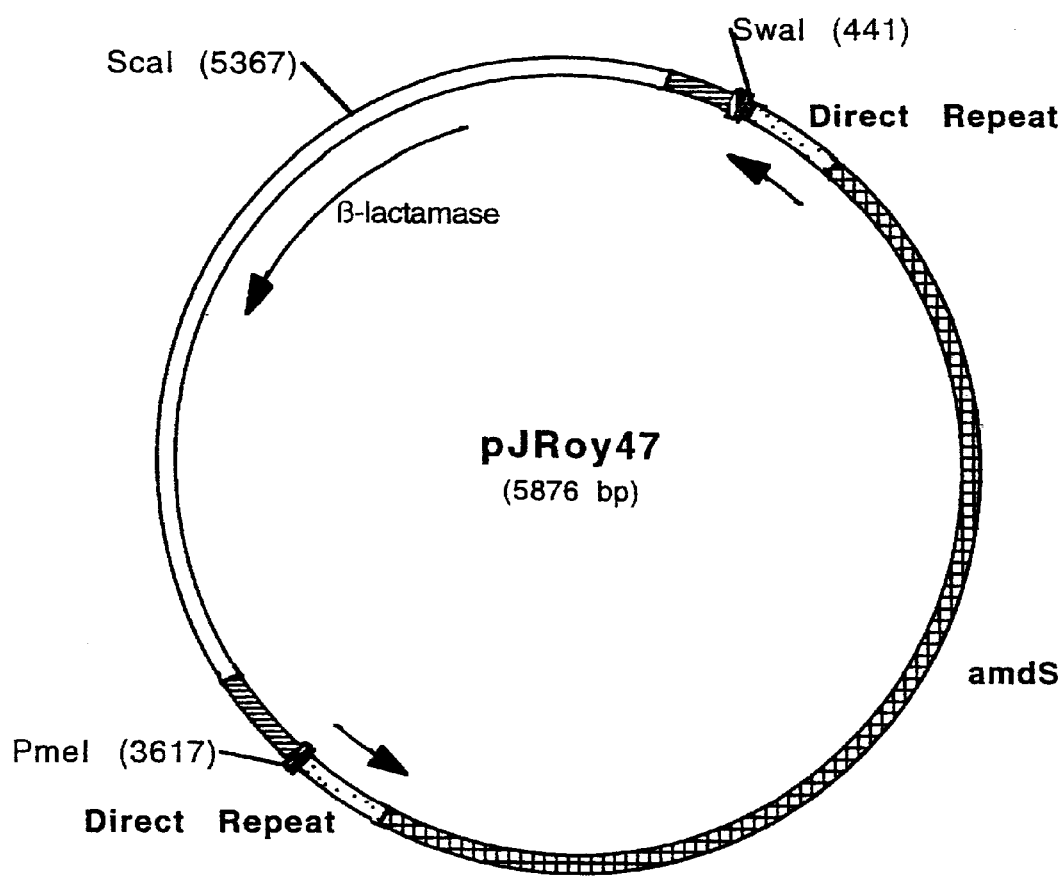
FIG. 4 shows a restriction map of pJRoy47.

Plasmid pJRoy44 was then digested with EcoRV and gel purified using the QiaQuick Gel Extraction Kit. A blunt 2.7 kb NsiI restricted fragment containing the *Aspergillus nidulans* amdS gene was ligated into EcoRV digested pJRoy44 to produce pJRoy47 (FIG. 4).

A 3.2 kb fragment containing the *Aspergillus nidulans* amdS gene flanked by 224 bp direct repeats, designed to facilitate recombination and removal of the amdS marker, was obtained by restricting pJRoy47 with PmeI, ScaI, and SwaI. This blunt ended DNA fragment was gel purified using a QiaQuick Gel Extraction Kit.

Figure 5:
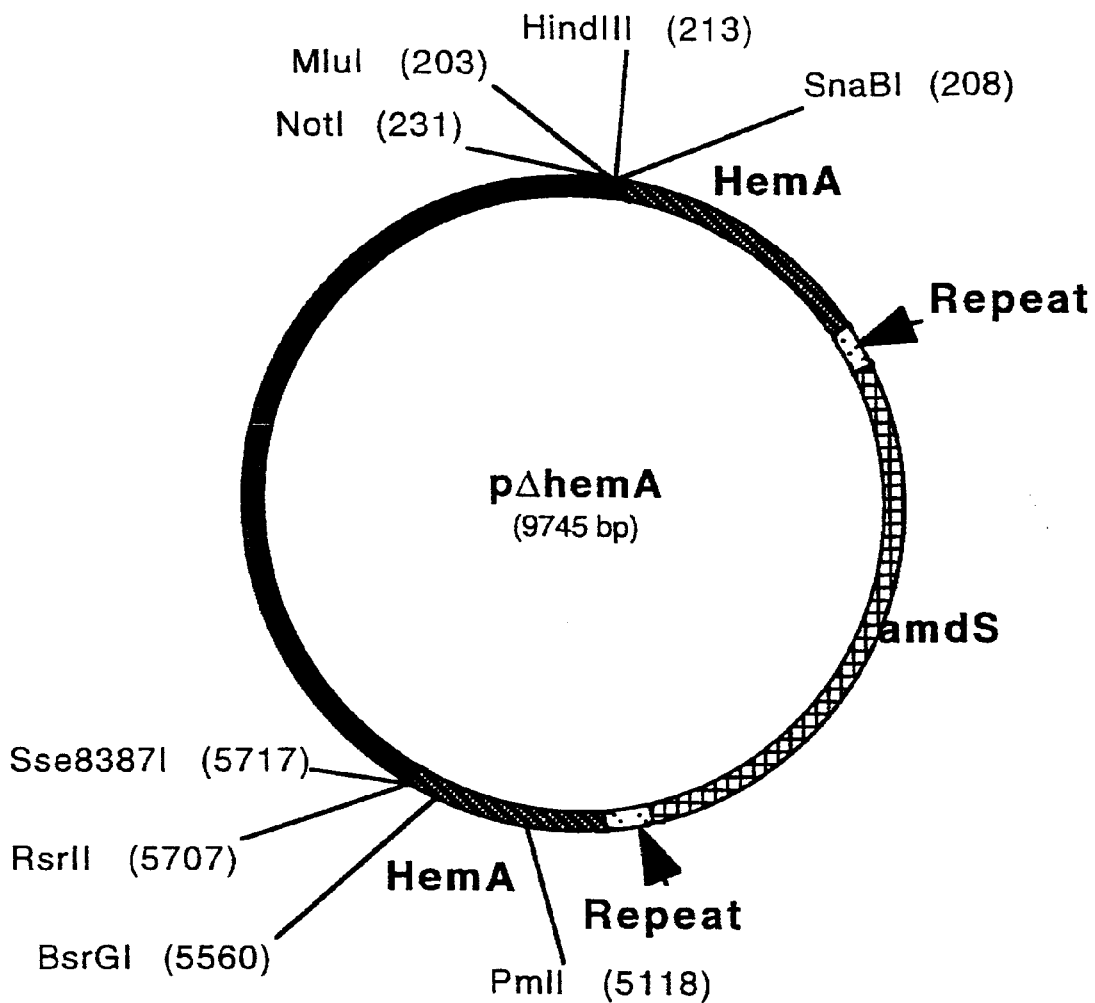
FIG. 5 shows a restriction map of pΔHemA.

The purified DNA fragment was cloned into pZL3-3 described in Example 4, restricted with NruI (to remove a 1616 bp fragment of the hemA ORF including the start codon), and ligated to produce pΔHemA (FIG. 5). The region of the hemA gene containing the deletion was sequenced to confirm the nature of the hemAΔ::amdS allele. Sequencing revealed that the hemA deletion removed coding sequence and destroyed the reading frame of the gene.

Example 6

Transformation of *Fusarium venenatum* with pΔHemA

*Fusarium venenatum* CC1-3 (MLY-3), a morphological mutant of Fusarium strain ATCC 20334 (Wiebe et al., 1991, *MycoL Research* 95: 1284–1288), was transformed with pΔHemA in order to replace the wild type hemA gene with the hemAΔ::amdS deletion allele.

Spores of *Fusarium venenatum* MLY-3 were generated by inoculating a flask containing 500 ml of RA sporulation medium with 10 plugs from a 1×Vogels medium plate (2.5% Noble agar) supplemented with 2.5% glucose and 2.5 mM sodium nitrate and incubating at 28° C., 150 rpm for 2 to 3 days. Spores were harvested through Miracloth (Calbiochem, San Diego, Calif.) and centrifuged 20 minutes at 7000 rpm in a Sorvall RC-5B centrifuge (E. I. DuPont De Nemours and Co., Wilmington, Del.). Pelleted spores were washed twice with sterile distilled water, resuspended in a small volume of water, and then counted using a hemocytometer.

Protoplasts were prepared by inoculating 100 ml of YEPG medium with 4×10⁷ spores of *Fusarium venenatum* MLY-3 and incubating for 16 hours at 24° C. and 150 rpm. The culture was centrifuged for 7 minutes at 3500 rpm in a Sorvall RT 6000D (E. I. DuPont De Nemours and Co., Wilmington, Del.). Pellets were washed twice with 30 ml of 1 M $MgSO_4$ and resuspended in 15 ml of 5 mg/ml of NOVOZYME 234™ (batch PPM 4356, Novo Nordisk A/S, Bagsvaerd, Denmark) in 1 M $MgSO_4$. Cultures were incubated at 24° C. and 150 rpm until protoplasts formed. A volume of 35 ml of 2 M sorbitol was added to the protoplast digest and the mixture was centrifuged at 2500 rpm for 10 minutes. The pellet was resuspended, washed twice with STC, and centrifuged at 2000 rpm for 10 minutes to pellet the protoplasts. Protoplasts were counted with a hemocytometer and resuspended in an 8:2:0.1 solution of STC:SPTC:DMSO to a final concentration of 2×10⁷ protoplasts per ml. The protoplasts were stored at −80° C., after controlled-rate freezing in a Nalgene Cryo 1° C. Freezing Container (VWR Scientific, Inc., San Francisco, Calif.).

Frozen protoplasts of Fusarium venenatum MLY-1 were thawed on ice. The transformation was conducted with protoplasts at a concentration of 2×10⁷ protoplasts per ml. Two hundred μl of protoplasts were mixed with 40 μg of pΔHemA plus 5 μl of heparin (5 mg per ml of STC) and incubated on ice for 30 minutes. Two mls of SPTC were added and the protoplasts were incubated for an additional 20 minutes at room temperature. Minimal medium overlay (50 ml) was added to the transformation reaction and the reaction was then plated onto two Minimal medium plates supplemented with 5 mM 5-aminolevulinic acid. 5-Aminolevulinic acid auxotrophy was determined by growing the primary transformants on Minimal medium lacking 5-aminolevulinic acid at room temperature for 12 days.

The transformation resulted in greater than 100 colonies. Screening of 30 primary transformants on Minimal medium lacking 5-aminolevulinic acid resulted in 19 strains whose growth appeared marginal. Ten of the transformants were chosen for Southern analysis.

Genomic DNA (10 μg) from each of the 10 transformants was prepared as described in Example 1 and restriction digested with EcoRV. The fragments were separated by 1% agarose gel electrophoresis using TAE buffer. DNA was transferred to a Nytran Plus nylon membrane in 10×SSC using a TurboBlot apparatus (Schleicher & Schuell, Keene, N.H.) according to the manufacturer's instructions. The membrane was prehybridized for 2 hours at 65° C. in 5×SSC, 0.1% sarkosyl, 0.02% SDS, 1% Genius blocking agent (Genius DIG Luminescent Detection Kit, Boehringer Mannheim, Indianapolis, Ind.), and 50% formamide in a Hybaid oven (Labnet, Woodbridge, N.J.). A DIG-labeled probe based on the 5' flanking region of the deleted hemA gene was prepared by PCR amplification of a DNA fragment from pΔHemA using primers 3-3243U and 3for.1 shown below.

3-3243: 5'-CCCTTCTAGGCAAGTCTATGG-3' (SEQ ID NO:13)

3for.1: 5'-CCGCAGCATGGCCGCAACTTG-3' (SEQIDNO:14)

The amplification reaction (50 μl) contained the following components: 50 ng of pΔHemA, 50 pmol of 3-3243U primer, 50 pmol of 3for. 1 primer, 5 μl of DIG labeled dATP, 1×DIG probe synthesis mix (Boehringer Mannheim, Indianapolis, Ind.), dCTP, dGTP, and dTTP, 1×Taq polymerase buffer (Perkin-Elmer Corp., Branchburg, N.J.), and 5 Units of Taq polymerase (Perkin-Elmer Corp., Branchburg, N.J.). The reaction was incubated in a Perkin-Elmer Model 480 Thermal Cycler programmed as follows: Cycle 1 at 95° C. for 5 minutes, 55° C. for 2 minutes, and 72° C. for 5 minutes: Cycle 2–30 each at 95° C. for 1 minute; 55° C. for 1 minute, and 72° C. for 1 minute; and a Soak cycle at 4° C. The reaction products were isolated on a 1.5% agarose gel using TAE buffer where a 300 bp product band was excised from the gel and purified using Qiaex II (Qiagen, Chatsworth, Calif.) according to the manufacturer's instructions.

The purified probe was first denatured in water at 4ng/ml by heating in a boiling water bath for 10 minutes and then was added to the hybridization solution described above. After overnight hybridization at 65° C., the membrane was washed in 2×SSC, 0.1% SDS for 10 minutes at room temperature followed by two washes in 0.5×SSC, 0.1% SDS for 15 minutes at 68° C. The washed membrane was then rinsed in 2×SSC, developed using a Genius DIG Luminescent Detection Kit according to the manufacturer's instructions, and exposed to Kodak Xomat AR film for approximately one hour.

Southern analysis of the transformants showed that 4 transformants contained only the hemAΔ::amdS allele and 6 contained both wild type and hemAΔ::amdS alleles. Two of the 4 transformants containing only the hemAΔ::amdS allele were spore isolated and then subjected to Southern analysis (as described above) in order to confirm the presence of the hemΔ::amdS allele and the absence of the wild type allele. Southern analysis showed that both transformants contained only the hemΔ::amdS allele. One of the transformants designated *Fusarium venenatum* 46-3 was chosen as a hemA mutant host strain.

Example 7

Rescue of the lethal hemA deletion phenotype by supplementation with 5-aminolevulinic acid The ability of 5-aminolevulinic acid to rescue the hemA deletion phenotype was determined by supplementation with 5-aminolevulinic acid.

A 250 mM stock solution of 5-aminolevulinic acid (Porphyrin Products, Logan Utah) was prepared in water, 0.22 micron filter sterilized, stored at −20° C. in the dark, and added to prepared media immediately prior to use or pouring. 5-Aminolevulinic acid, ranging in concentration from 0.005 mg/ml to 0.3 mg/ml, was added to Minimal medium agar or YEG liquiq medium. *Fusarium venenatum* 46-3 was cultivated in these media for 7 days at 28° C. The YEG liquid medium was agitated at 200 rpm.

The results showed that concentrations of 5-aminolevulinic acid as low as 30 μM (5.0 μg/ml) were sufficient to rescue the auxotrophic phenotype when added to Minimal medium agar. Growth in liquid YEG medium required slightly higher concentrations (up to 1 mM).

Example 8

Construction of pJRoy54HemA

Plasmid pJRoy54HemA was constructed to contain the wild type hemA allele and a expression cassette driving the expression of a heterologous gene encoding the *Thermomyces* (Humicola) *lanuginosus* lipase known as LIPOLASE™

Figure 6:
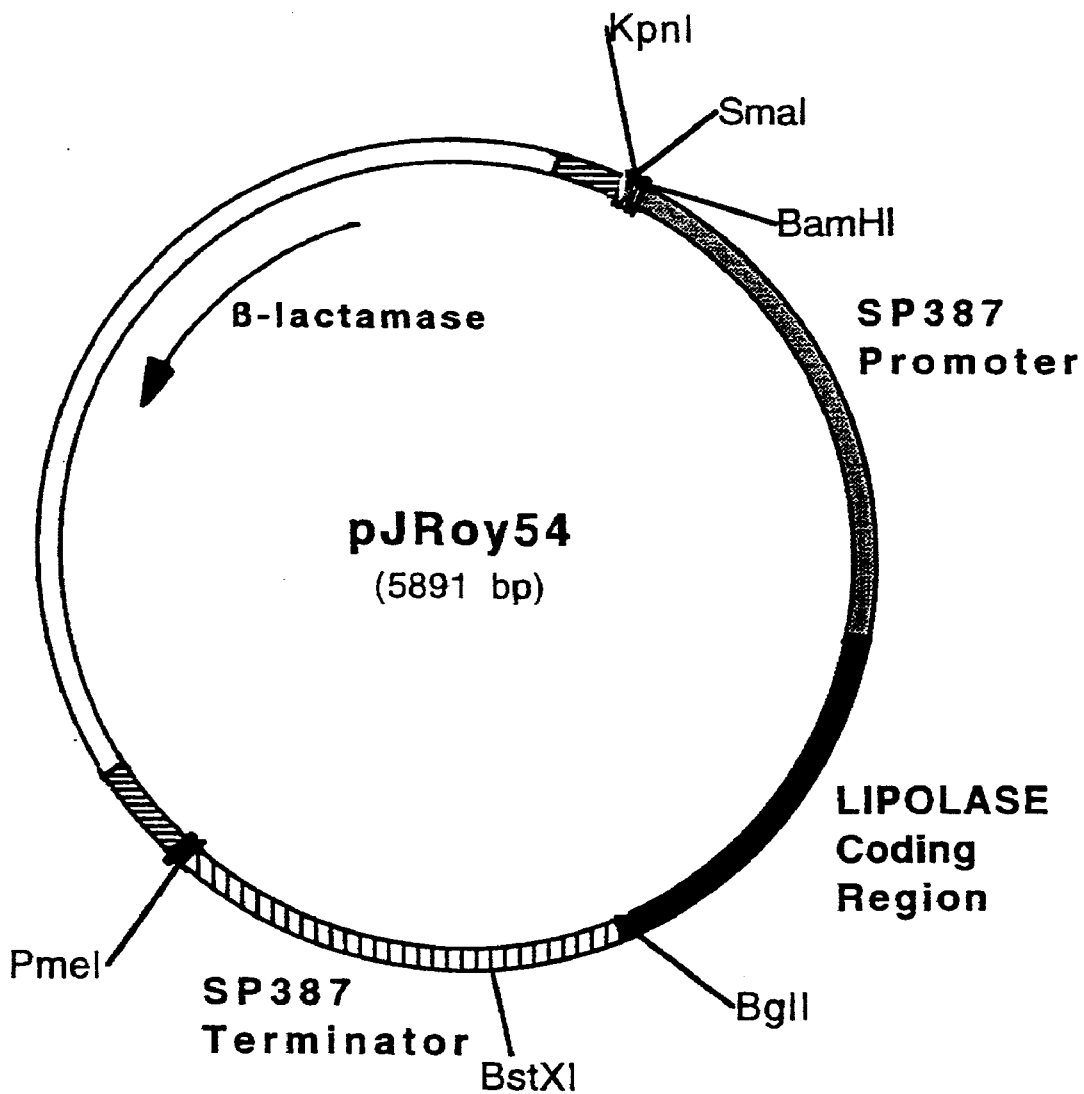
FIG. 6 shows a restriction map of pJRoy54.

(Novo Nordisk A/S, Bagsvaerd, Denmark). Specifically, a 3.5 kb fragment containing the Fusarium venenatum hemA gene including its native promoter and terminator was obtained by digesting pZL3-3 with BamHI and filling the recessed ends with Klenow enzyme. This blunt ended DNA fragment was gel purified using a QiaQuick Gel Extraction Kit.

pJRoy54 was constructed to contain an expression cassette containing the LIPOLASE™ gene driven by the Fusarium oxysporum SP387 promoter and terminator. First plasmid pNEB193 was restricted with the blunt cutter HindII and gel purified using the Qiaquick Gel Extraction Kit. Then a blunt ended LIPOLASE™ expression cassette driven by the *Fusarium oxysporum* SP387 promoter and terminator was obtained as described in WO 96/00787 and ligated into pNEB 193 resulting in plasmid pJRoy54 (FIG. 6).

Figure 7:
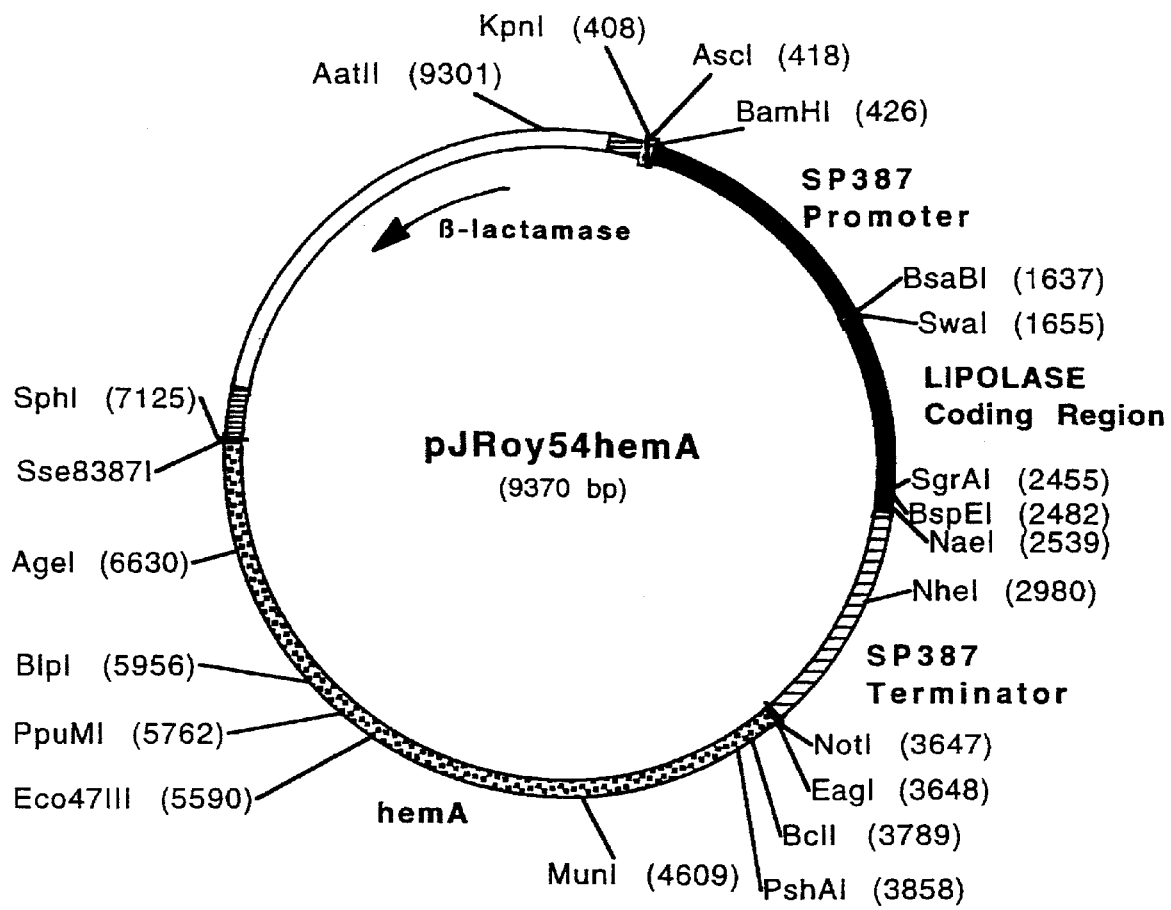
FIG. 7 shows a restriction map of pJRoy54HemA.

The purified 3.5 kb fragment containing the *Fusarium venenatum* hemA gene was cloned into PmeI digested pJRoy54 to produce pJRoy54HemA (FIG. 7). Sequencing of this plasmid confirmed the presence of the hema gene.

Example 9

Transformation with pJRoy54HemA

Transformations were performed with protoplasts prepared from *Fusarium venenatum* 46-3 using the procedure described in Example 6. The protoplasts were transformed with 50 μg of pJRoy54HemA, plated onto Minimal medium lacking 5-aminolevulinic acid, and incubated at room temperature. Transformed colonies were apparent after ten days incubation. Seven transformants were obtained with pJRoy54HemA, while no colonies 2 5 appeared on the "no DNA" control plates, i e., Fusarium venenatum 46-3 as a control.

The seven transformants were found to be 5-aminolevulinic acid prototrophs. DNA was isolated from all seven transformants (designated HL 1–7) and submitted to Southern analysis according to the procedure described in Example 6. The results demonstrated that they contained at least one copy of the intact hema gene, in addition to the hemA deletion allele. This data confirmed that the hema deletion phenotype can be rescued by transformation with the wild type hemA gene.

In addition, transformants HL1–7 were grown for 7 days at 28° C. in 125 ml shake flasks containing 25 ml of M400 medium. Lipase activity was measured according to the following procedure. The assay substrate was prepared by diluting 1:5 the stock substrate (10 μl of p-nitrophenylbutyrate per ml DMSO) into MC buffer (3 mM $CaCl_2$-0.1M MOPS pH 7.5) immediately before use. Standard LIPOLASE® (Novo Nordisk A/S, Bagsvaerd, Denmark) contained 1000 LU per ml of 50% glycerol-0.66 mM $CaCl_2$-33 mM Tris pH 7.5 and was stored at −20° C. Standard LIPOLASE® was diluted 1/100 in MC buffer just before use. Broth samples were diluted in MC buffer and 100 μl aliquots of the diluted broth samples were pipetted into 96-well microtiter dishes followed by 100 μl of diluted substrate. The absorbance at 405 nm was recorded as a function of time. Broth lipase units/ml (LU/ml) were calculated relative to the LIPOLASE® standard. All transformants produced lipase activity at day 7.

Deposit of Biological Materials

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
| --- | --- | --- |
| *E. coli* DH5a pZL3-3 | NRRL B-21855 | October 20, 1997 |

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. An isolated nucleic acid sequence encoding a polypeptide having 5-aminolevulinic acid synthase activity, selected from the group consisting of:
   (a) a nucleic acid sequence encoding a polypeptide having an amino acid sequence which has at least 90% identity with the amino acid sequence of SEQ ID NO. 2;
   (b) a nucleic acid sequence having at least 90% homology with the nucleic acid sequence of SEQ ID NO. 1;
   (c) a nucleic acid sequence which hybridizes under high stringency conditions with (i) the nucleic acid sequence of SEQ ID NO. 1 or (ii) its complementary strand; or a subsequence thereof of at least 100 nucleotides;
   (d) a subsequence of (a), (b), or (c), wherein the subsequence encodes a polypeptide fragment which has 5-aminolevulinic acid synthase activity.

2. The nucleic acid sequence of claim 1, which encodes a polypeptide having an amino acid sequence which has at least 90% identity with the amino acid sequence of SEQ ID NO. 2.

3. The nucleic acid sequence of claim 2, which encodes a polypeptide having an amino acid sequence which has at least 95% identity with the amino acid sequence of SEQ ID NO. 2.

4. The nucleic acid sequence of claim 1, which encodes a polypeptide comprising the amino acid sequence of SEQ ID NO. 2.

5. The nucleic acid sequence of claim 1, which encodes a polypeptide consisting of the amino acid sequence of SEQ ID NO. 2, or a fragment thereof which has 5-aminolevulinic acid synthase activity.

6. The nucleic acid sequence of claim 5, which encodes a polypeptide consisting of the amino acid sequence of SEQ ID NO. 2.

7. The nucleic acid sequence of claim 1, which has at least 90% homology with the nucleic acid sequence of SEQ ID NO. 1.

8. The nucleic acid sequence of claim 7, which has at least 95% homology with the nucleic acid sequence of SEQ ID NO. 1.

9. The nucleic acid sequence of claim 1, which has the nucleic acid sequence of SEQ ID NO. 1.

10. The nucleic acid sequence of claim 1, wherein the nucleic acid sequence hybridizes under high stringency conditions with (i) the nucleic acid sequence of SEQ ID NO. 1 or (ii) its complementary strand; or a subsequence thereof of at least 100 nucleotides.

11. The nucleic acid sequence of claim 10, wherein the nucleic acid sequence hybridizes under high stringency conditions with (i) the nucleic acid sequence of SEQ ID NO. 1 or (ii) its complementary strand.

12. The nucleic acid sequence of claim 1, which is contained in the plasmid pZL3-3 which is contained in *E. coli* NRRL B-21855.

13. An isolated nucleic acid sequence comprising a nucleic acid sequence having at least one mutation in the mature polypeptide coding sequence of SEQ ID NO. 1, in which the mutant nucleic acid sequence encodes a polypeptide having the amino acid sequence of SEQ ID NO. 2.

14. A nucleic acid construct comprising the nucleic acid sequence of claim 1 operably linked to one or more control sequences which direct the production of the polypeptide in a suitable expression host.

15. A recombinant expression vector comprising the nucleic acid construct of claim 14, a promoter, and transcriptional and translational stop signals.

16. A recombinant host cell comprising the nucleic acid construct of claim 14.

17. A method for producing a polypeptide having 5-aminolevulinic acid synthase activity comprising (a) cultivating the host cell of claim 16 under conditions suitable for production of the polypeptide; and (b) recovering the polypeptide.

\* \* \* \* \*